(12) United States Patent
Ridings

(10) Patent No.: US 7,350,921 B2
(45) Date of Patent: Apr. 1, 2008

(54) IQUEVISION: ANIMATED / VISION TESTING SYSTEM

(75) Inventor: Phillip Vincent Ridings, Southaven, MS (US)

(73) Assignee: Phillip V. Ridings, Southaven, MS (US)

( * ) Notice: Subject to any disclaimer, the term of this patent is extended or adjusted under 35 U.S.C. 154(b) by 376 days.

(21) Appl. No.: 10/805,633

(22) Filed: Mar. 22, 2004

(65) Prior Publication Data
US 2005/0225720 A1 Oct. 13, 2005

Related U.S. Application Data

(60) Provisional application No. 60/480,319, filed on Jun. 23, 2003.

(51) Int. Cl.
*A61B 3/02* (2006.01)
(52) U.S. Cl. .................. 351/237; 351/239; 351/246
(58) Field of Classification Search ............. 351/200, 351/205, 222, 246, 239, 237, 243
See application file for complete search history.

(56) References Cited

U.S. PATENT DOCUMENTS

| | | | | |
|---|---|---|---|---|
| 5,229,972 A | * | 7/1993 | Kondo et al. | 365/185.11 |
| 5,946,075 A | * | 8/1999 | Horn | 351/246 |
| 6,108,634 A | * | 8/2000 | Podnar et al. | 351/200 |
| 6,203,157 B1 | * | 3/2001 | Lee | 351/242 |
| 6,228,038 B1 | * | 5/2001 | Claessens | 351/210 |
| 6,238,049 B1 | * | 5/2001 | Griffin et al. | 351/243 |
| 2002/0024634 A1 | * | 2/2002 | Fink et al. | 351/237 |
| 2002/0042580 A1 | * | 4/2002 | Alster et al. | 351/211 |

* cited by examiner

*Primary Examiner*—Hung X. Dang
(74) *Attorney, Agent, or Firm*—Phillip V. Ridings

(57) ABSTRACT

A device for performing in eye test includes a display for animated visual acuity letters and sealable dynamic letters, a computer to control the display and to link to a patient database, and the display having at least a contrast sensitivity of 400:1, a true rez visual acuity letter of 1°, a screen resolution of 1024 and a ambient light 768>4500K.

7 Claims, 34 Drawing Sheets

Figure 9A:
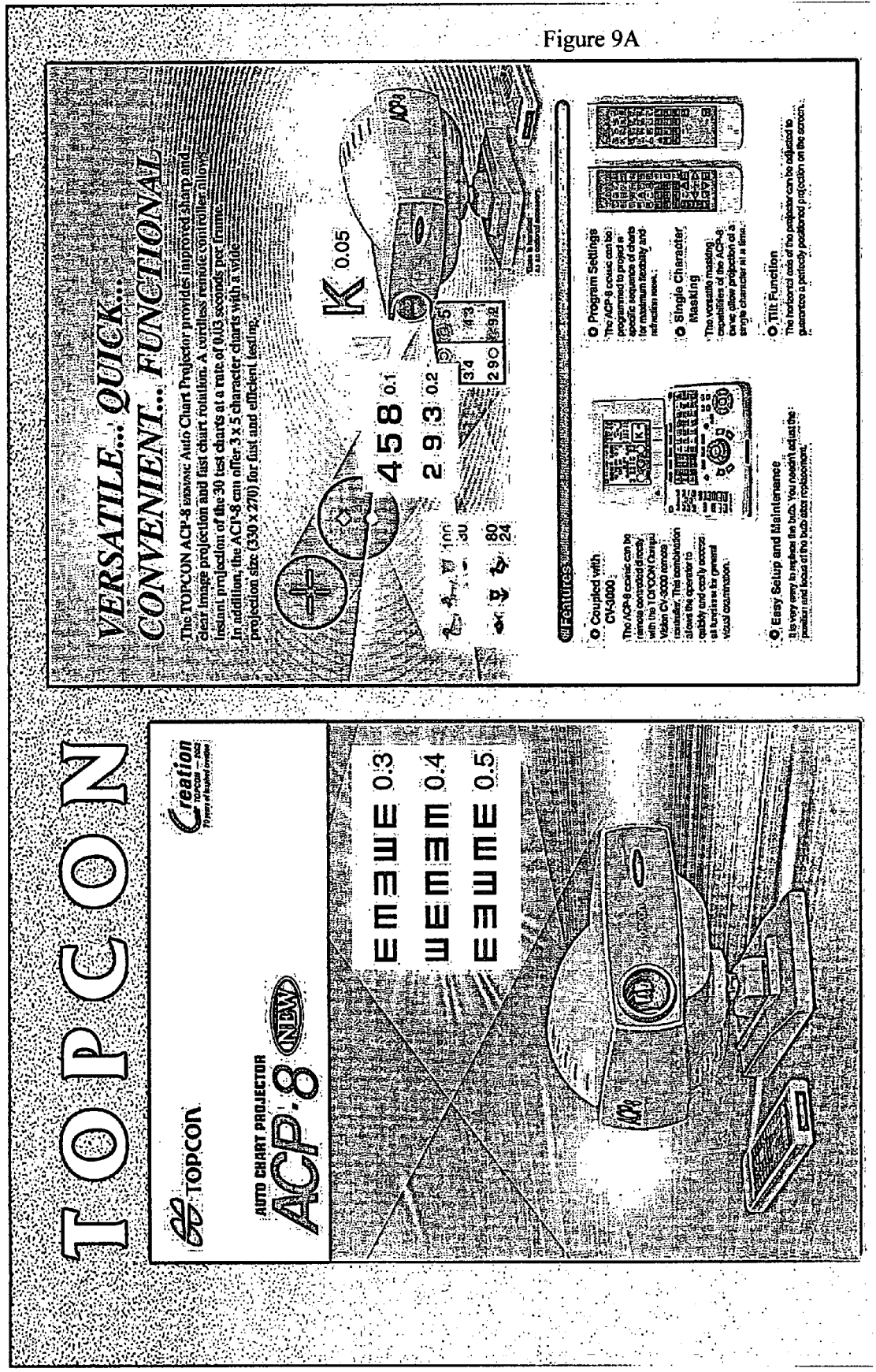

Multiple Operating Systems on a Unix Server (Fig.2)

Legend
A - iQue A.VTS configured on a Unix Server
B - Cross Platform System include: Windows, Macintosh and RedHat Lunix
C - Desktop Icon for Visual Records and Patient Records
D- Wireless Keayboard / Mouse Control for Internet Access or Patient Data
E - Opional Palm Pilot / Mouse Pointer
F - PC Tablet
G -Hard Wired or Wireless Network to Linked Screens
H- Wall mounted Hi-Rez Screen
I- Hi-Rez 17" - 50" Screens with 500:1 or Higher Contrast Level
J- Kiosk interface Menu Style for easy file access $\tan \Theta = h/d$ $\tan 5' = h/6m; \; h = 8.73mm$ The digial minimum formula is:
  400:1 Contrast Sensitivity or >
  @ 1° true rez visual acuity letters
  @ min screen resolution of 1024x768 or >
  4500K ambient light or >.

$\tan \Theta = h/d$          400:1> ⊖ @ 1°TR
                              SR 1024 x 768 >/4500K>
$\tan 5' = h/6m; \; h = 8.73mm$ 400:1 CS
Resolution ) 1°
1024 x 768
Ambient 4500K

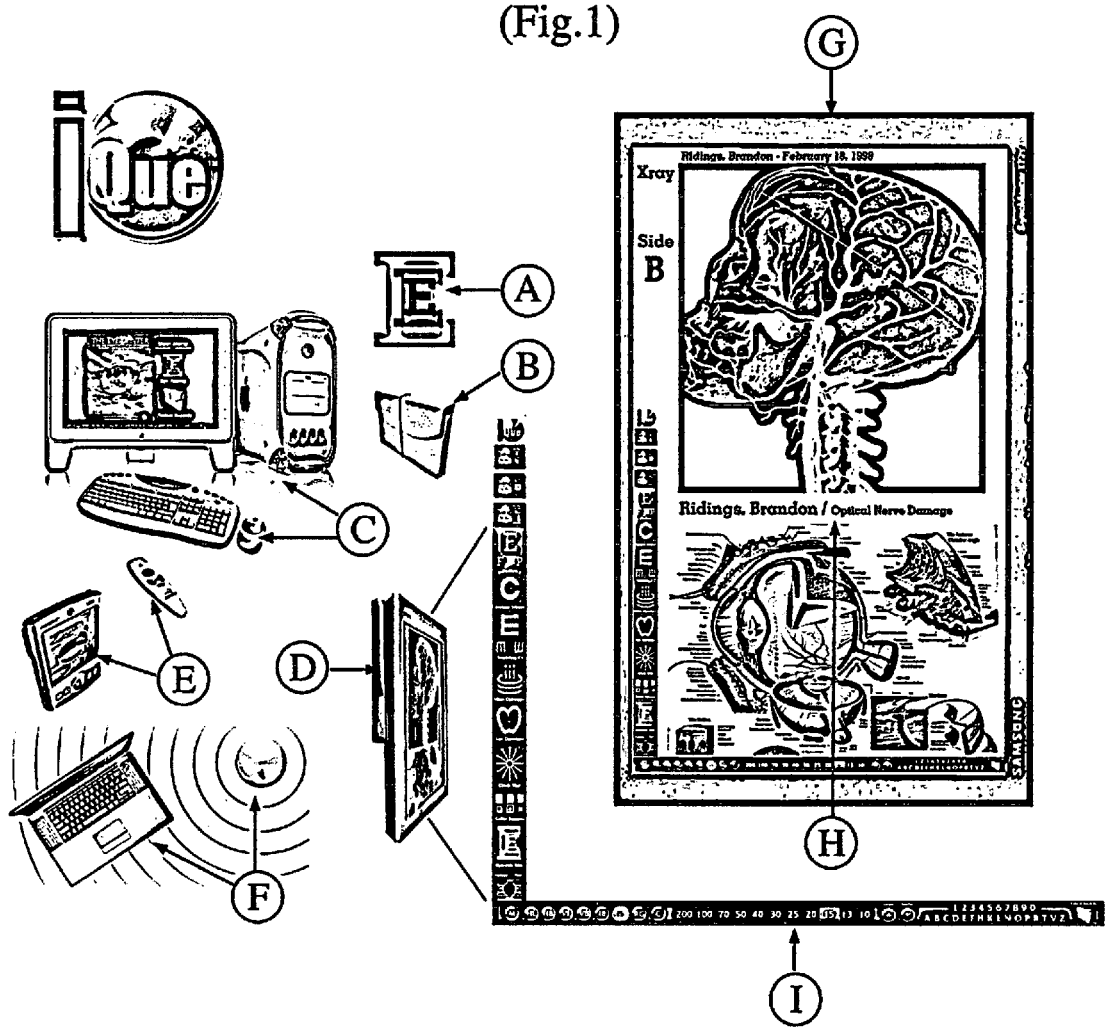

Multiple Operating Systems on a Unix Server
(Fig.2)

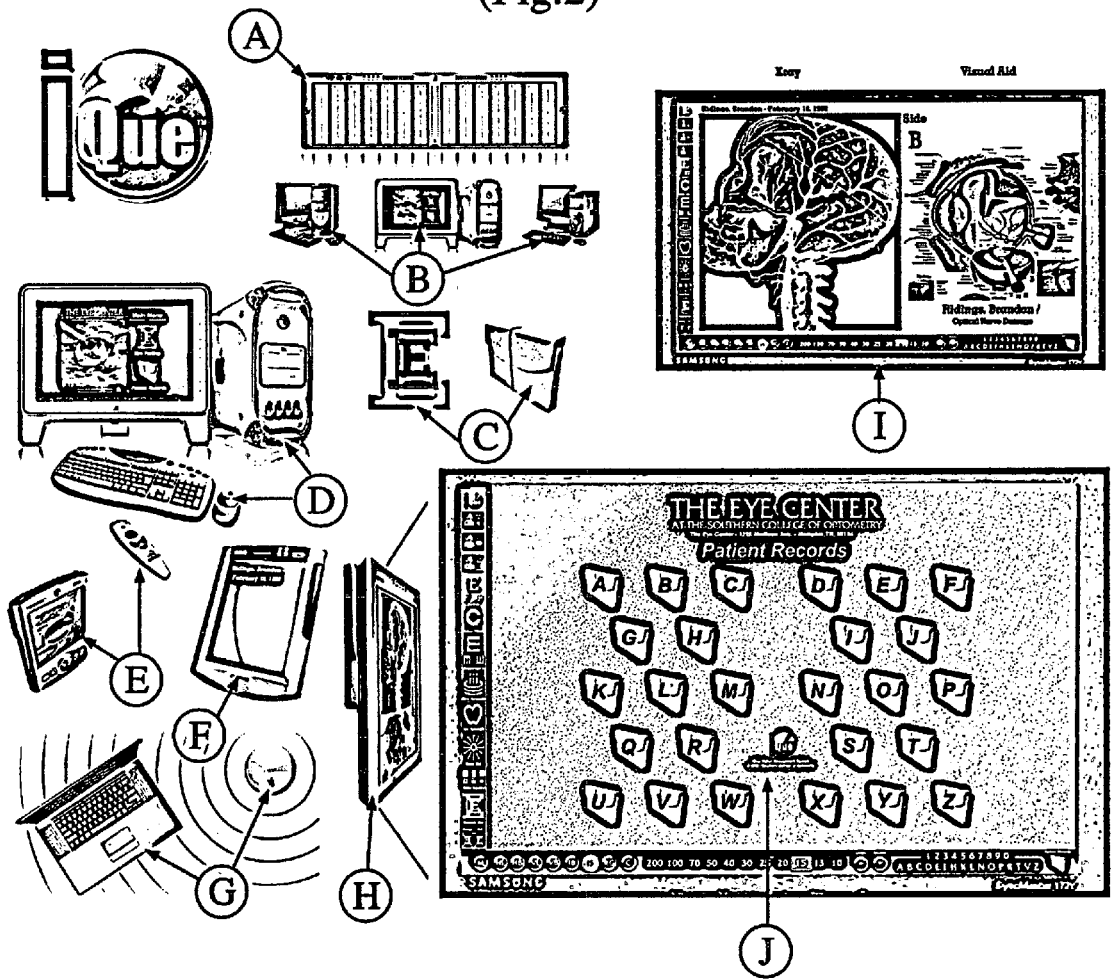

Legend
A - iQue A.VTS configured on a Unix Server
B - Cross Platform System include: Windows, Macintosh and RedHat Lunix
C - Desktop Icon for Visual Records and Patient Records
D- Wireless Keayboard / Mouse Control for Internet Access or Patient Data
E - Opional Palm Pilot / Mouse Pointer
F - PC Tablet
G -Hard Wired or Wireless Network to Linked Screens
H- Wall mounted Hi-Rez Screen
I- Hi-Rez 17" - 50" Screens with 500:1 or Higher Contrast Level
J- Kiosk interface Menu Style for easy file access

Multiple Operating Systems on a Unix Server
(Fig.3)

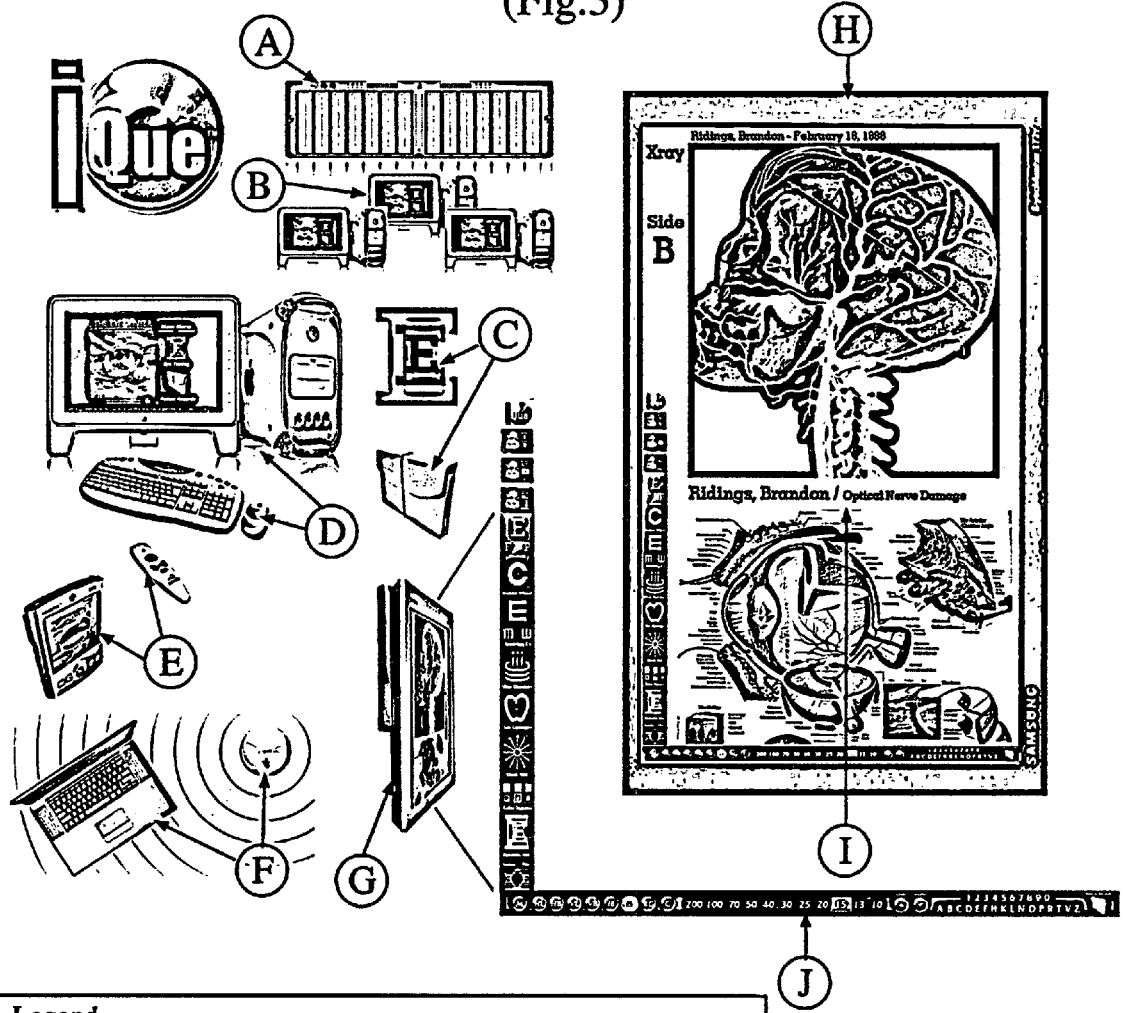

Legend
A - iQue A.VTS configured on a Unix Server
B - 250 Users 125 Host Files
C - Desktop Icon for Visual Records and Patient Records
D- Wireless Keayboard / Mouse Control for Internet Access or Patient Data
E - Opional Palm Pilot / Mouse Pointer
F -Hard Wired or Wireless Network to Linked Screens
G- Wall mounted Hi-Rez Screen
H- Hi-Rez 17" - 50" Screens with 500:1 or Higher Contrast Level
I- Kiosk Interface showing Screen projection
J- Kiosk interface Menu Style for easy file access

Portable / Wireless Connection to a Unix Server
(Fig.4)

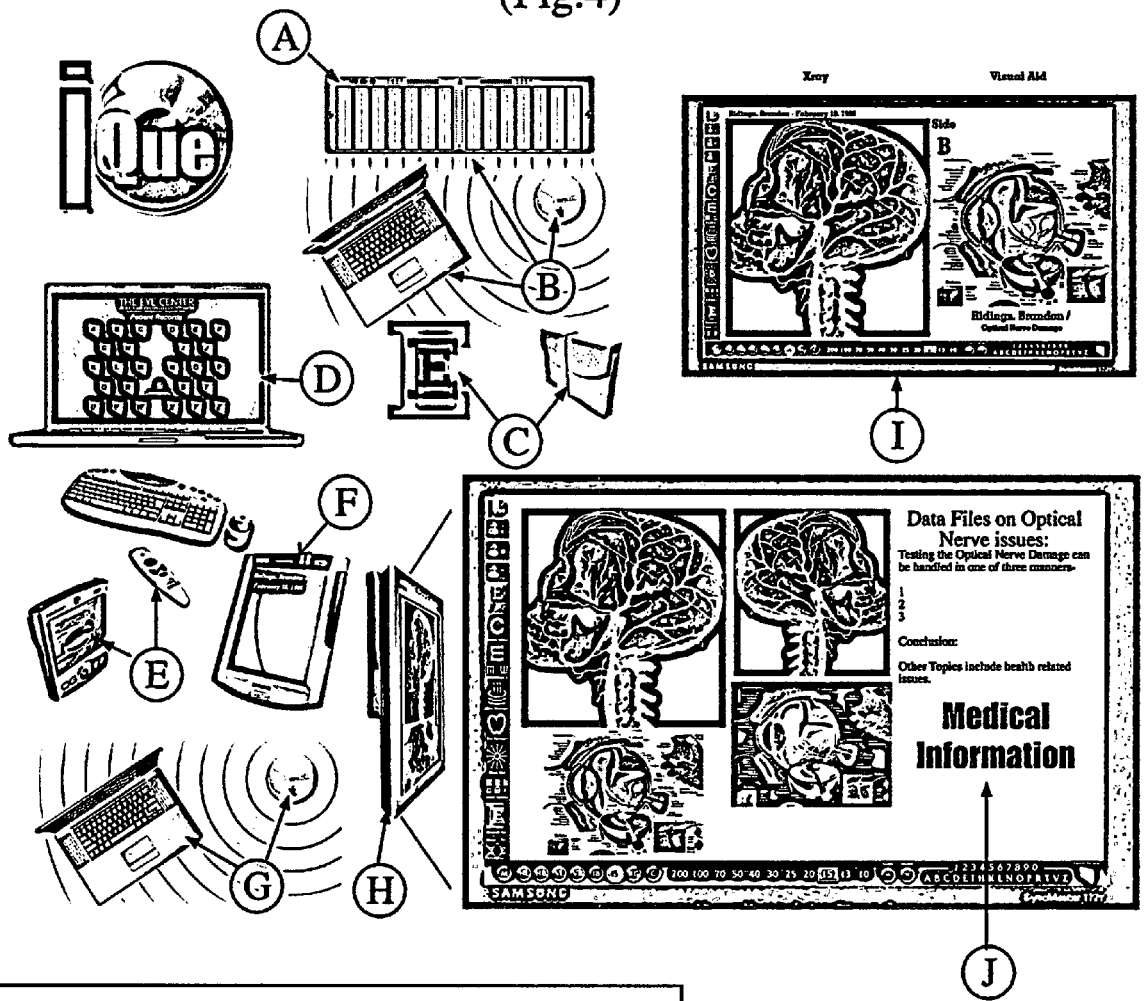

Legend
A - iQue A.VTS configured on a Unix Server
B - Wireless conection to server
C - Desktop Icon for Visual Records and Patient Records
D- Portable Laptop showing Patient files
E - Opional Palm Pilot / Mouse Pointer
F- PC tablet
G -Hard Wired or Wireless Network to Linked Screens
H- Wall mounted Hi-Rez Screen
I- Hi-Rez 17" - 50" Screens with 500:1 or Higher Contrast Level
J- Kiosk Interface showing Screen projection

Internet Based Home Therapy System
(Fig.5)
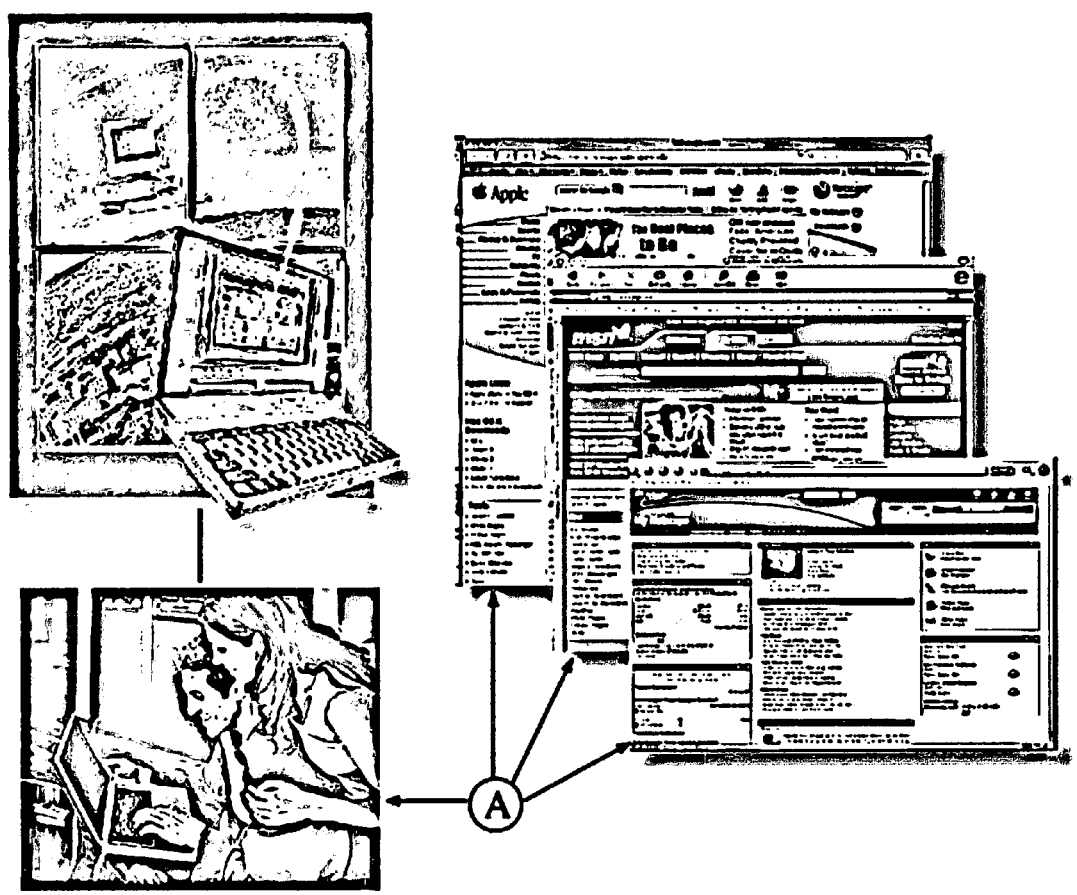
Legend
A- Using any Internet Browser: A patient can access simple therapy test as long as the monitor meets resolution and size requirements

Unix Server Benefits and Connections
(Fig.6)
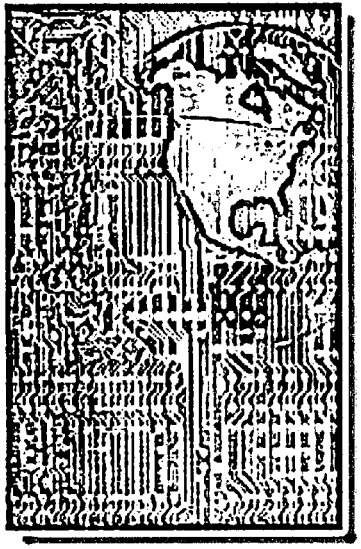
Legend
A - Client Servers
B - Individual Office systems
C - Portable Laptop and Wireless
D - To Home Therapy
E - HIPAA Compliant with "Off-Site" Backup and Storage on all Medical Records
F - Internet Global Connection
G - Company support and connetions to Head Quarters for iQue A/VTS -via internet.
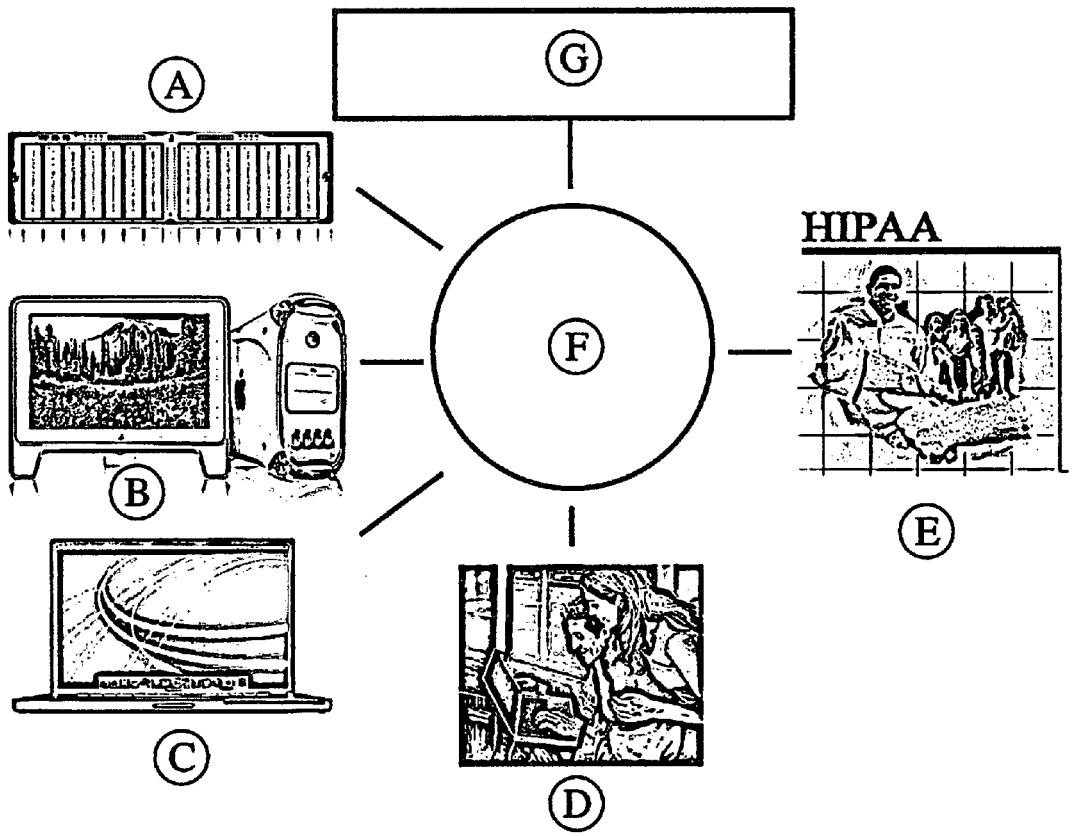

Functionality & Menu Control
(Fig. 7)
Main Menu

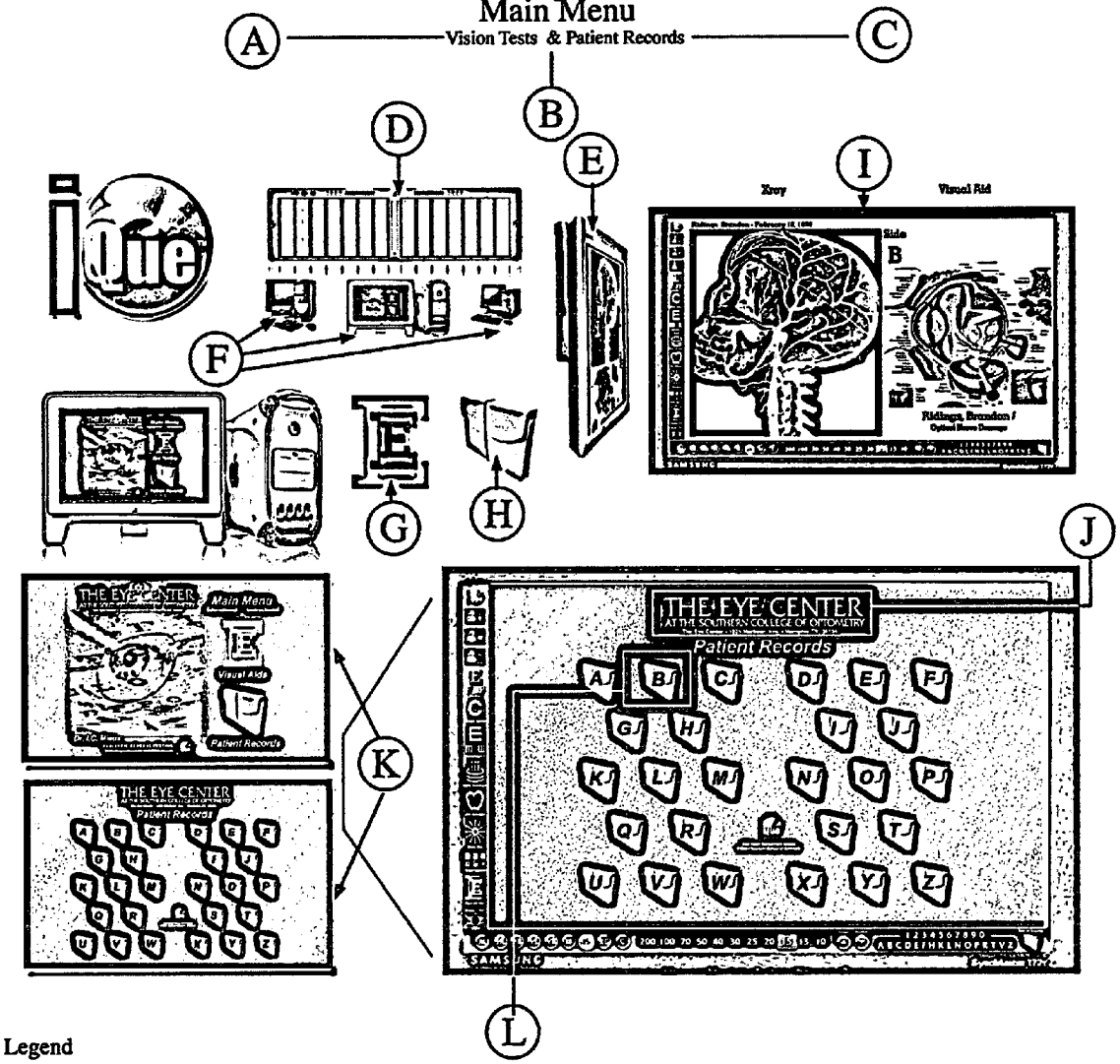

Legend
A - Include: Charts, Graphs, Photos Illustrations, Xrays and Video Movies and more
B - Include: Internet Servicing w/ Audio /VideoConferencing
C - Include: Administrative Data, Financial, Privacy, Medical History, Exam Profile and Medical Release forms
D- Unix Server
E - Wall mounted Hi-Rez Screen
F - Multiple OS's
G- Desktop Icon for Visual Records
H- Desktop Icon for Patient Records
I- Hi-Rez 17" - 50" Screens with 500:1 or Higher Contrast Level
J- Customized Screens for Doctors preference / samples include but are not limited to these designs:
K- Kiosk Mode Style Menus Simple Touch the Screen or use a mouse to select the desired results.
L- Using the kiosk menu system gives the Doctor complete control over the entire exam procedure.

Measurement Formula for 20/20 Vision
$$\tan \Theta = h/d$$
$$\tan 5' = h/6m;\ h = 8.73mm$$
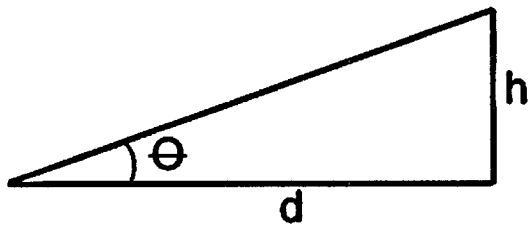
Figure 8
Digital Acuity Vision Testing Formula (DAVTF)
The digial minimum formula is:
- 400:1 Contrast Sensitivity or >
- @ 1° true rez visual acuity letters
- @ min screen resolution of 1024x768 or >
- 4500K ambient light or >.
$\tan \Theta = h/d$
$\tan 5' = h/6m;\ h = 8.73mm$
$$\frac{400:1 > \Theta\ @\ 1°TR}{SR\ 1024 \times 768 >/4500K>}$$
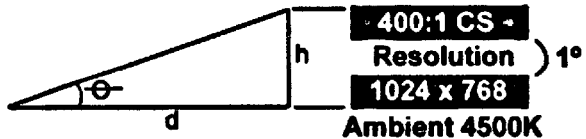

Figure 9C
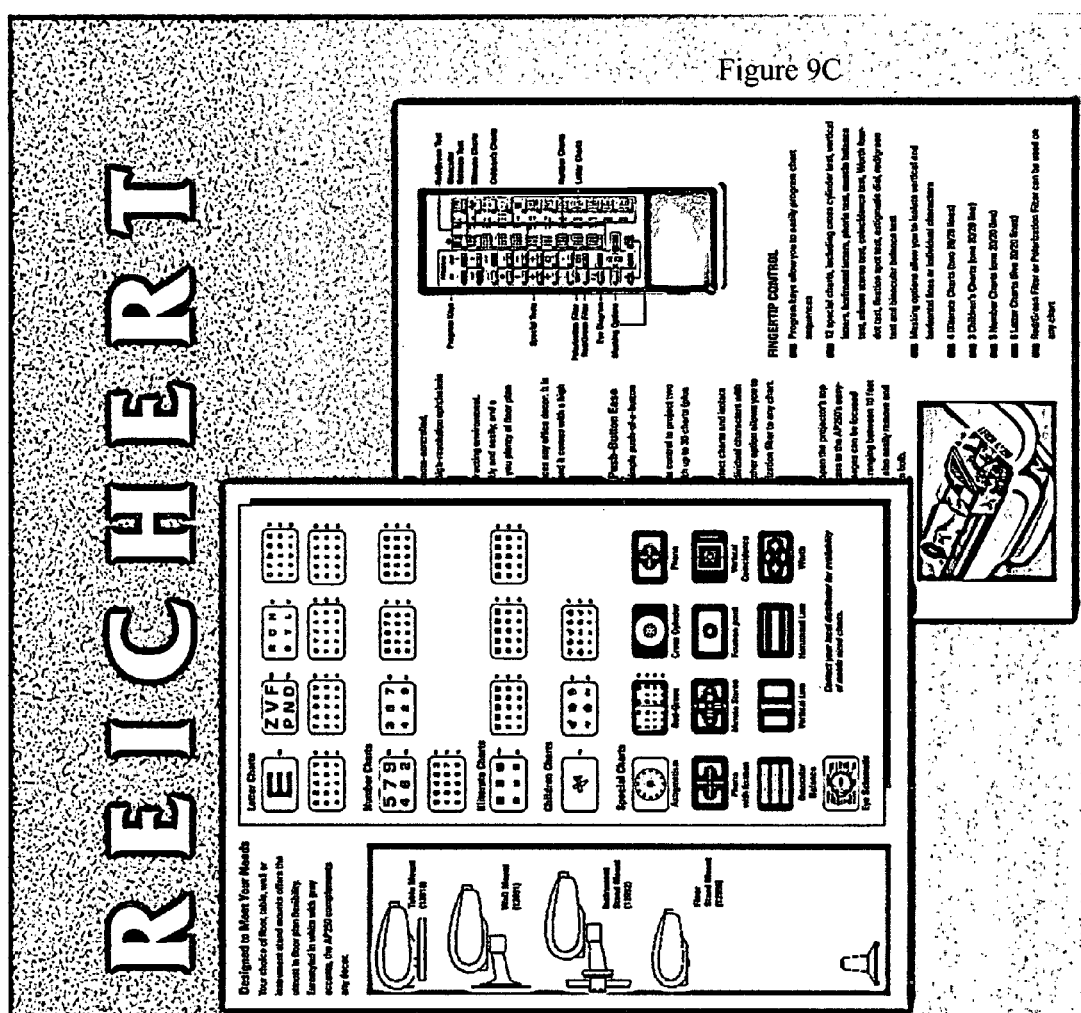
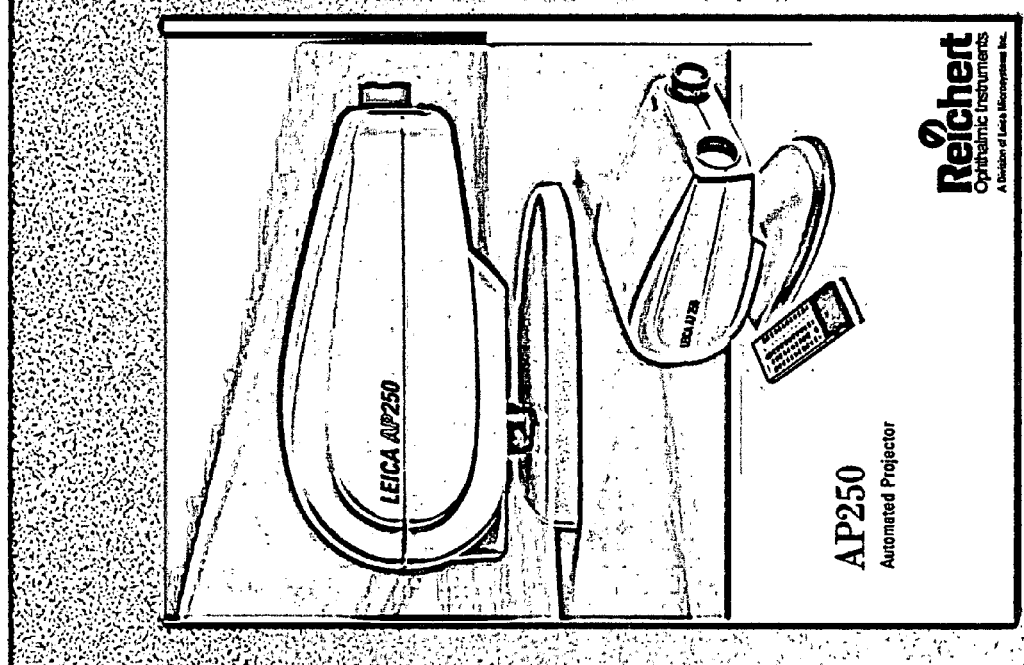

Figure 11

OBSERVATIONS

Bulb Life
Bulbs & Halogen Bulbs
Halogen Bulbs burn at 3000 - 3500K
Brightness of the bulb during its life
2 - 3 years - $50 - $550 Replacement

Slide Test
Easy Access to different Slides
Damage due to wear and tear
Limited Number of Tests
Fuzzy Letter over any distance
No Color Screening
Winter Heater
Not Much Fun...

Room Lighting
Silver Oxide (Gray) Screens
Contrast Lighting < 250:1
Room Lights 4000 - 6500K
Dim the room lights to see the screen
No Real World Lighting

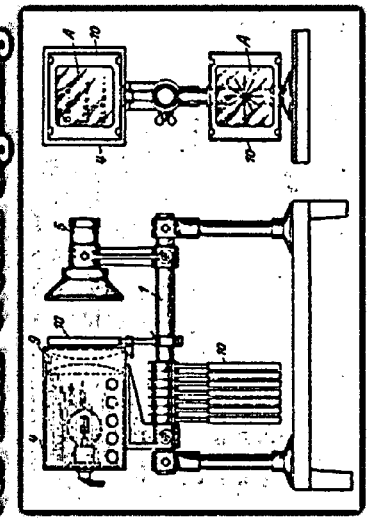

Figure 19A:
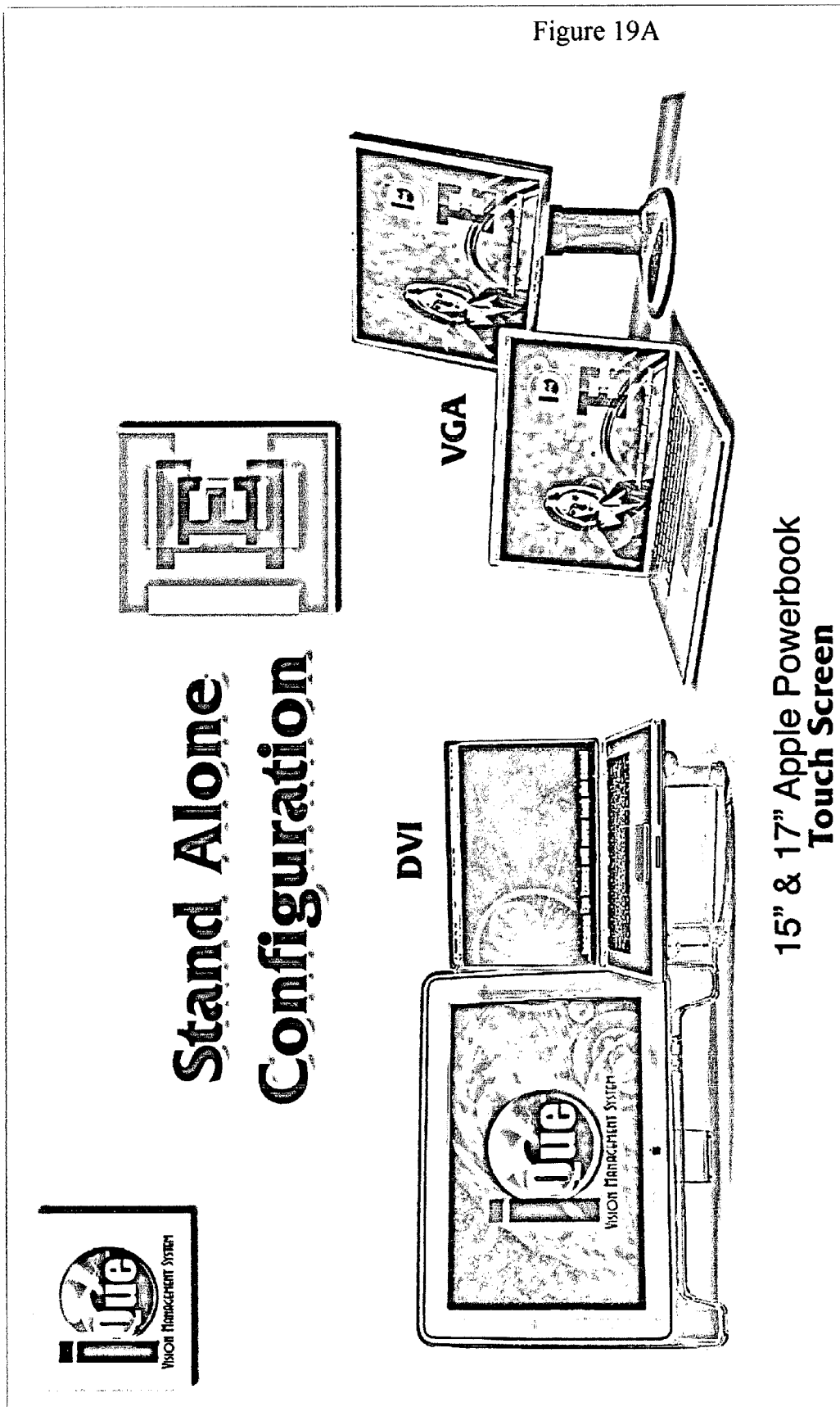
Figure 19C:
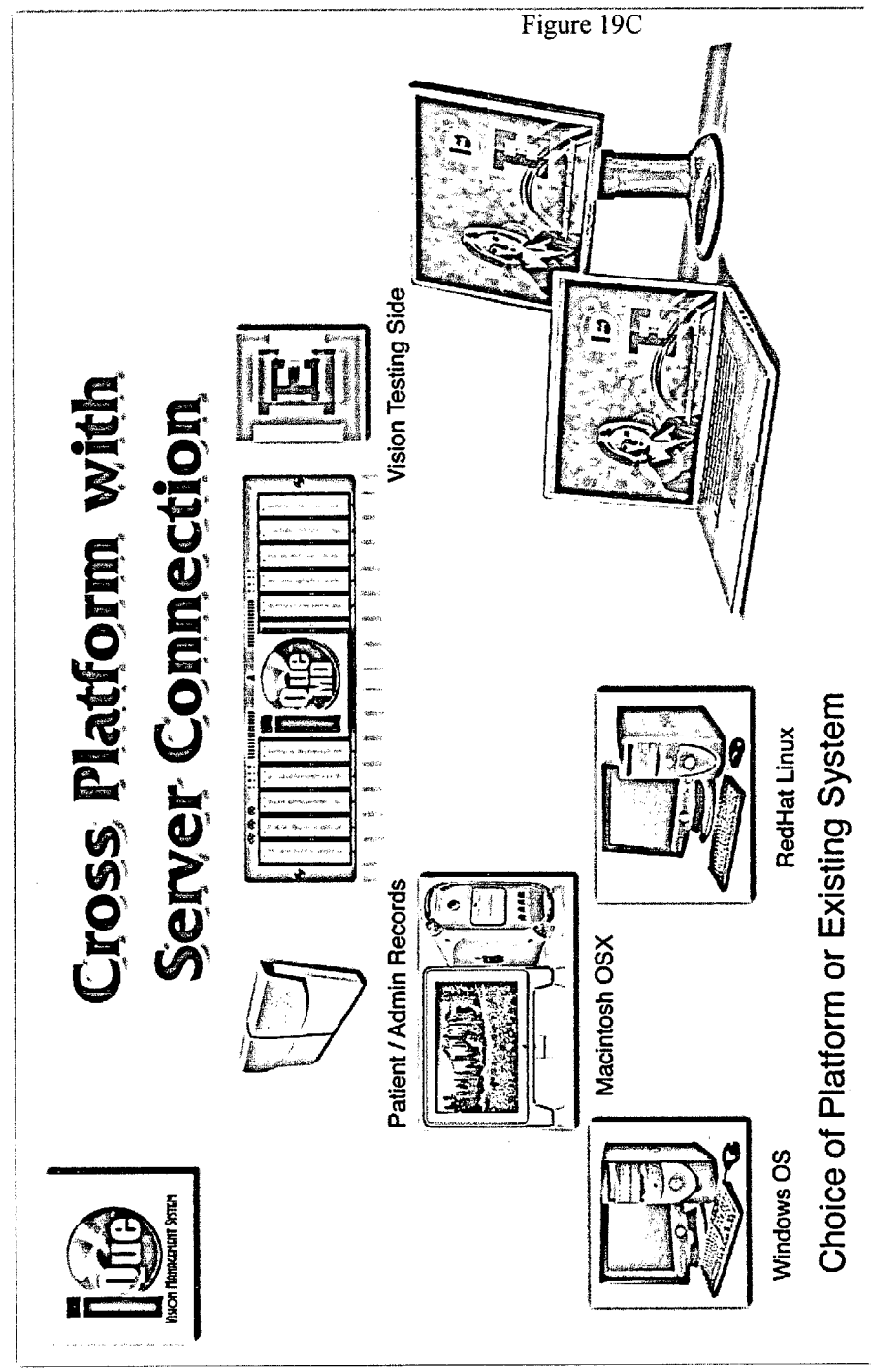
Figure 19D:
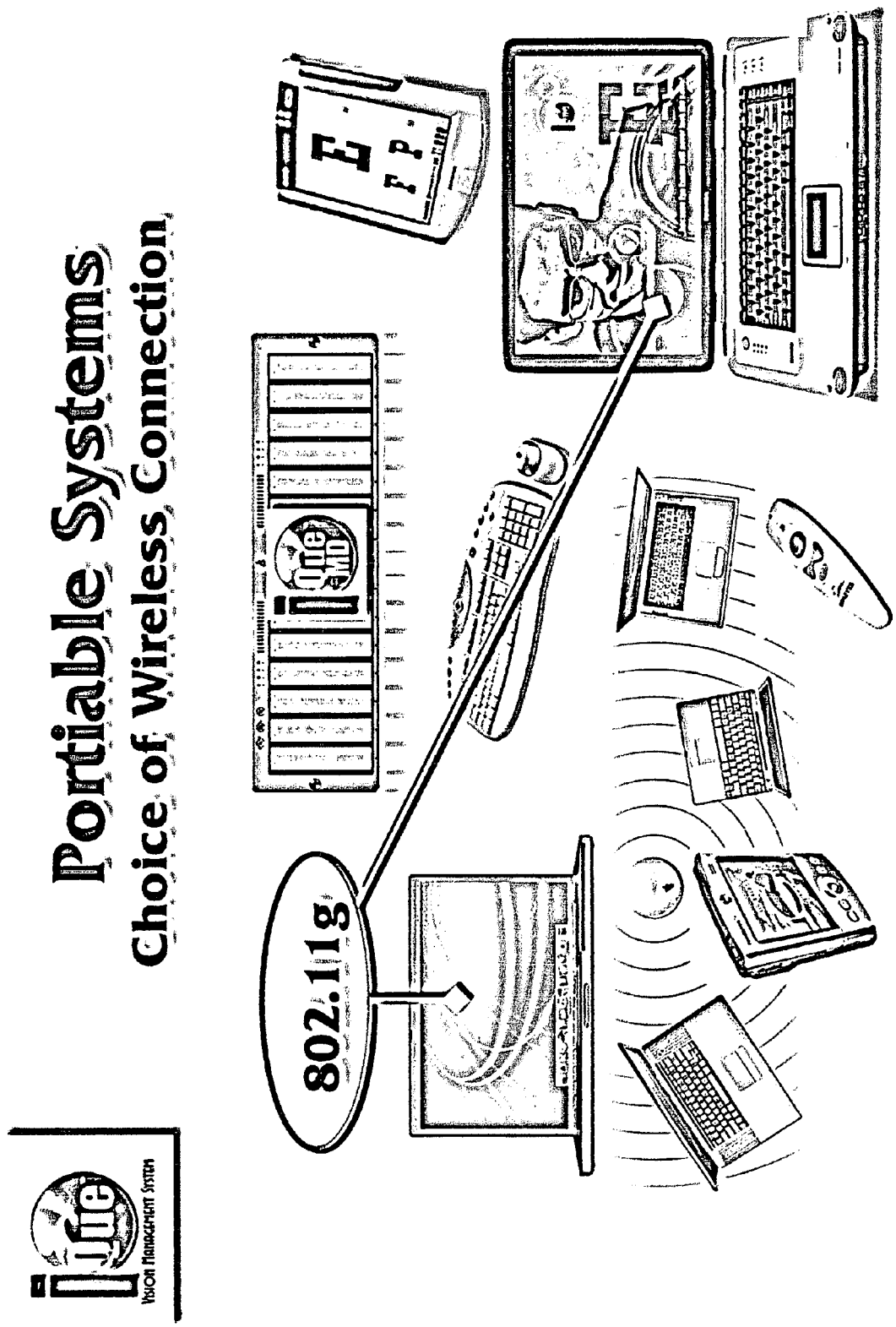
Figure 19E:
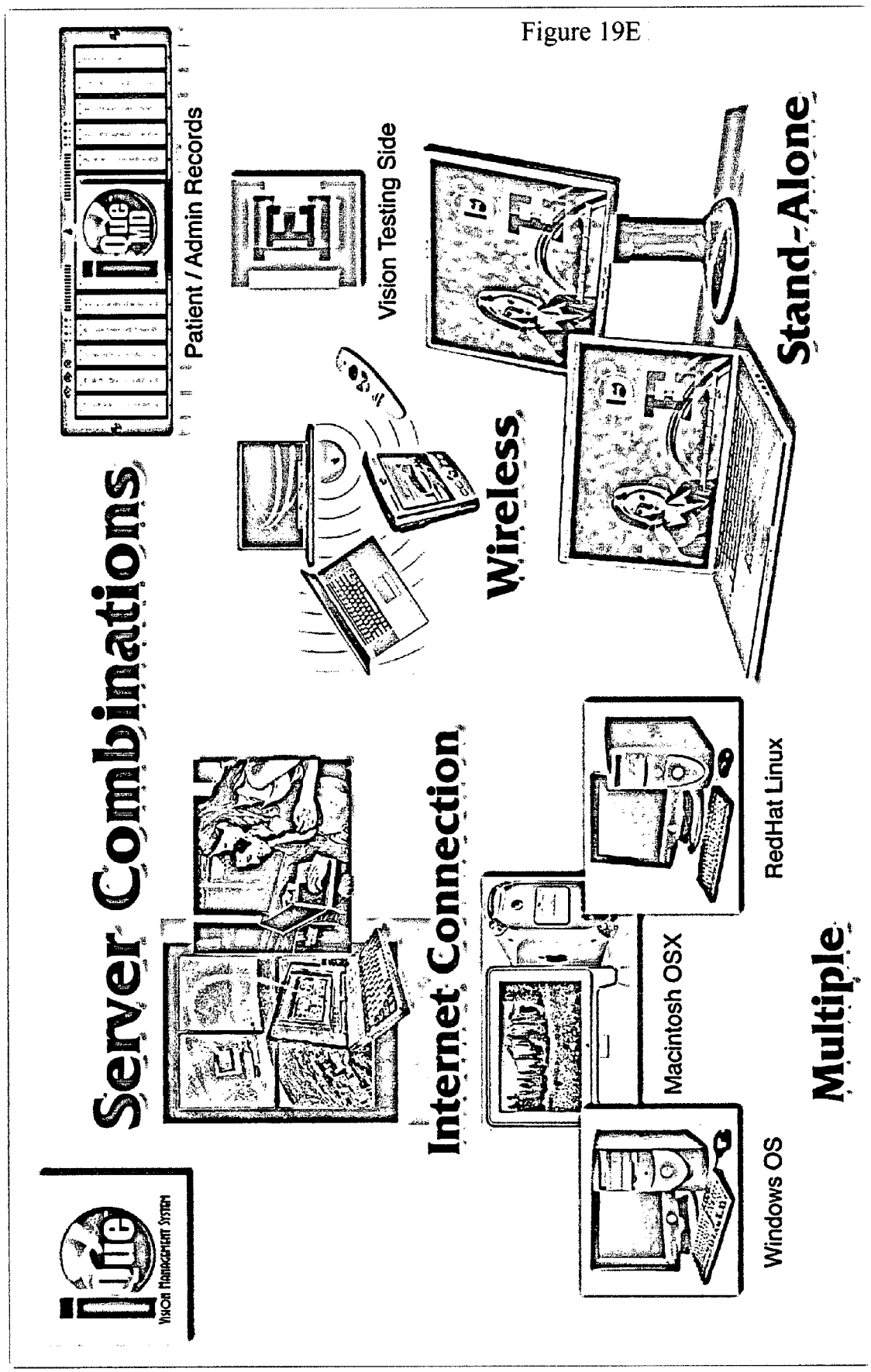

Figure 19B
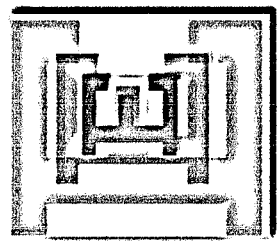
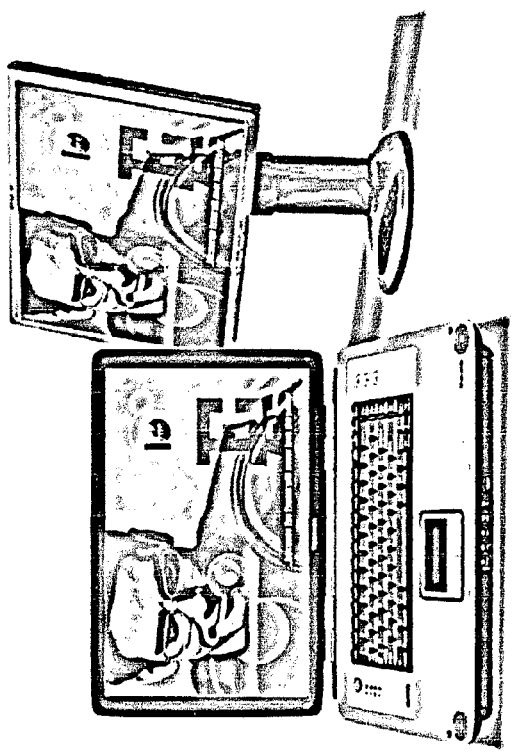
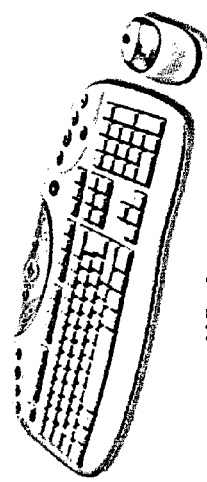

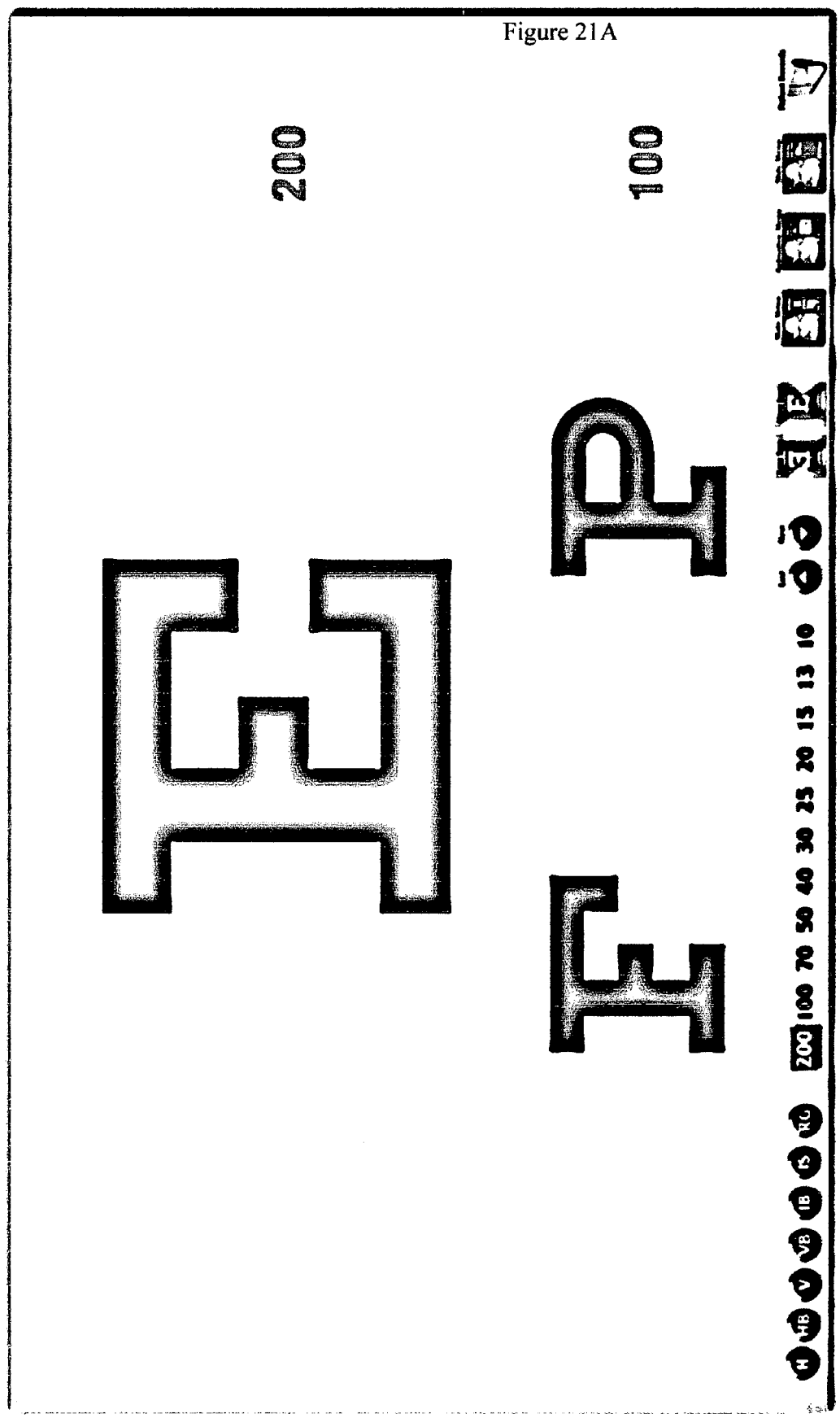

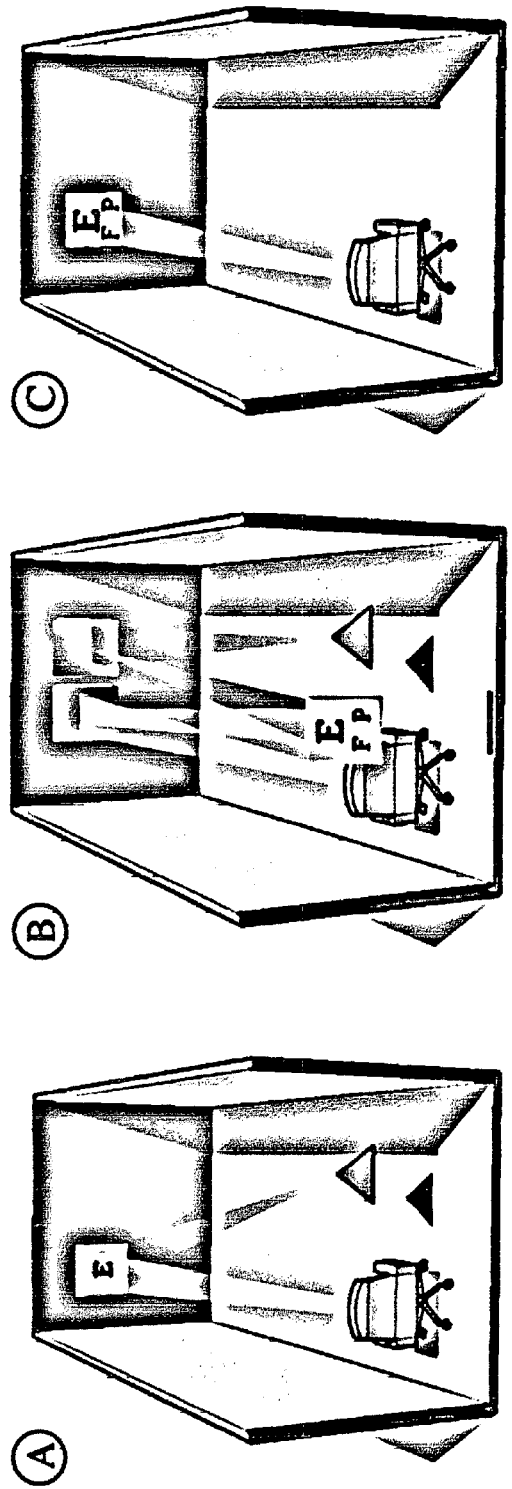
Figure 22. Projection Systems vs iQueVision A/VTS
Legend
A- Patients Veiw vs Projection in a 20ft room
B- Patients Veiw vs Projection in a 10ft Mirrored room
C- Patients Veiw with iQueVision Monitor Sreen in a 10 or 20ft room

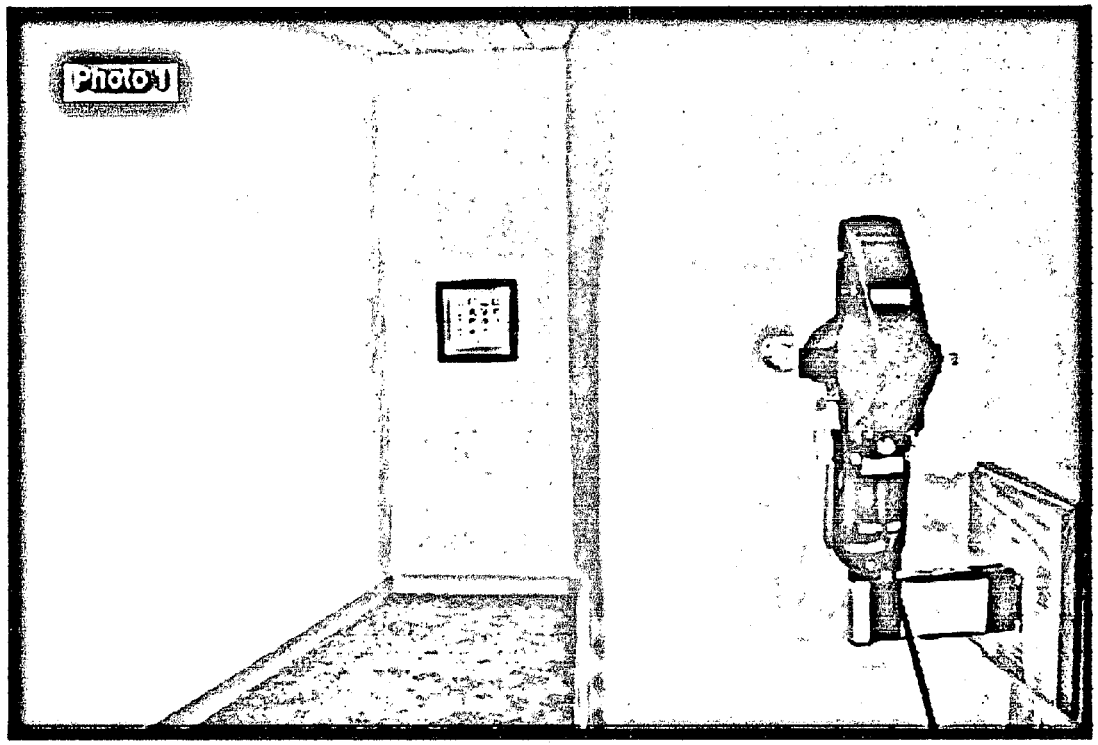
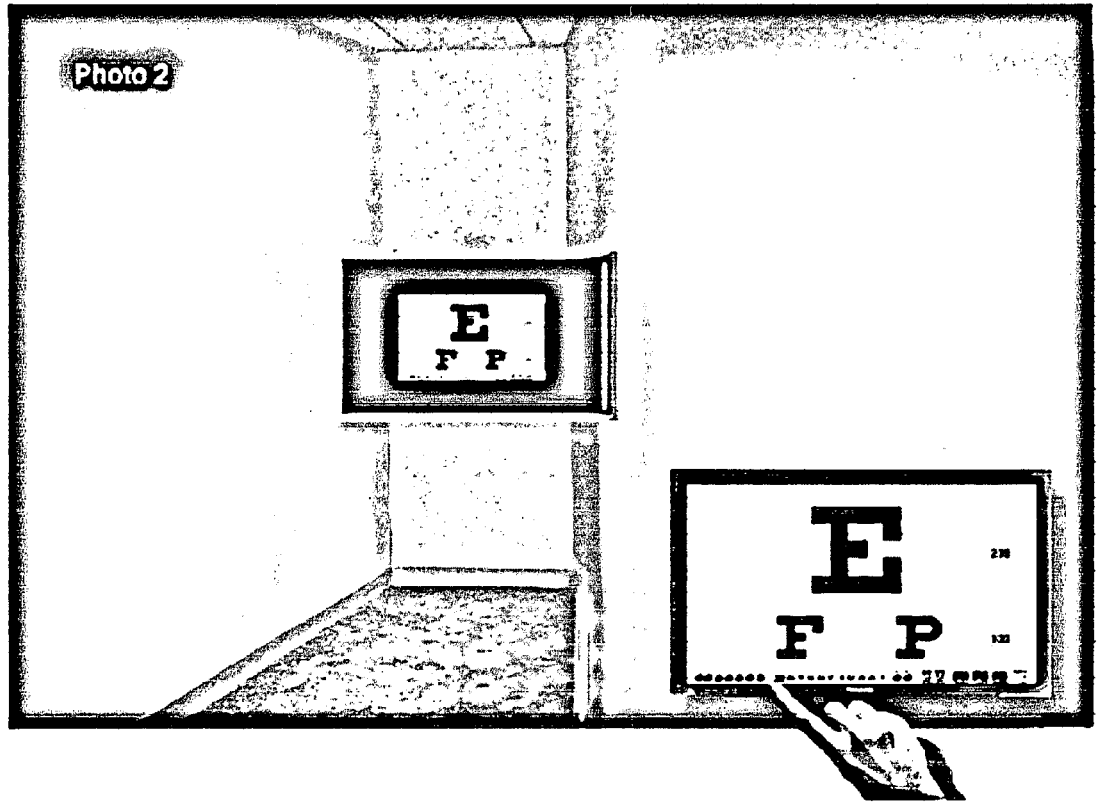
Figure 23

IQUEVISION: ANIMATED / VISION TESTING SYSTEM

CROSS-REFERENCE TO RELATED APPLICATION

60/480,319, DATED Jun. 23, 2003 Title: Animated/Vision Testing System

BACKGROUND

1. Field of Invention

This invention relates to field of Visual Acuity Testing, specifically to animated/slide computerized vision testing system and a new "Digital Formula" in the measurement of visual acuity for vision testing on not one but three cross-platform computer systems to achieve accurate and consistent results.

2. Background

This invention relates to eye testing, specifically using a pre-programmed database computer/portable laptop/tablet PC/Unix based computer server, controlled by an active matrix touch screen (kiosk), electronic personal data assistance (PDA) Keyboard to display an animated eye chart testing system on a high-resolution computer monitor, television or plasma screen for the purpose of testing visual acuity in humans. With the iQueVision: Animated/Vision Testing System (A/VTS) a skilled doctor can quickly check visual acuity with a larger variety of tests then any other projection or computerized system in use today. iQueVision: A/VTS gives any doctor instant access via kiosk/touch screen computer/laptop/tablet PC/palm pilot/computer keyboard and mouse and voice recognition to any number of product materials, educational tools, visual tests and testing methods. These methods include animated eye charts, slide charts, instructional slides and videos, educational slides and videos as well as HTML/XML internet access and patient files all in one pre-programmed computer/portable laptop/tablet PC/Unix based computer server or PDA. Also unique in this design is the ability to give the doctor control over the same software using a wired or wireless network with touch screen capabilities. Another bonus feature is that a patient can also have access to key testing a home using any computer that fits the testing standard through this internet home vision therapy system.

3. History or Description of Prior Art

Vision testing today is based on individual paper charts, pictures, slide projection systems and a few computer software programs. While each of these methods address a specific vision screening area they all have to be constantly replaced or updated due to wear and tear under general use. The most frustrating aspect of each of these vision testing methods is that they are all independent of each other and can not be incorporated together because of their design or hardware limitation. The idea behind all of these testing methods is that everyone should be able to see and identify a 3½" letter using Dr. Snellen's measurements at 20 ft. in distance. Some computerized vision testing systems may appear to present a bigger problem for non-computer literate doctors; however, many doctors who don't like the idea of using complex computer systems might be more inclined to use this low tech method for testing that gives them instant access via a pre-programmed database controlled by a touch screen (kiosk) and linked with a computer/server, tablet pc, PDA or keyboard/mouse. The only operational knowledge requirement for iQueVision A/VTS is an average household push button appliance that also uses touch screen or touch pad technology, thus eliminating the need to understand complex computer/laptop/Unix server systems. This is a low tech answer of building a touch screen program using one active and one passive monitor system puts 21st century technology into doctor's hands without the wear and tear and technical problems associated with existing products. In a closed looped program (kiosk) the doctor simply turns on the system and is presented with a touch screen set of buttons to choose from. A custom designed menu allows the doctor to instantly pull up any acuity test they desire.

After 2 years of research it has become quite apparent that the current vision testing tools, projection systems and testing methods are out dated and over 60 years old. The same bulb system used in the old projection systems patented in 1922 (see FIG. 8) and updated in 1948 are still being used today with one exception—brighter bulbs and the current projection systems also use an illuminated hand held remote. What sets the iQueVision: A/VTS system apart from other projection systems today is the doctor can turn the room lights back on because of a digital discovery called: "Contrast Sensitivity" or contrast ratio. This has been a key issue of controversy since the late 40s and one we would like to change, where doctors have been forced to dim the lights in order to administer a visual acuity test. As mentioned "Contrast Sensitivity" on a normal bulb projection system is well below 250:1. Even with modern improvements such as the halogen bulbs it may reach a full light ratio of 250:1 but nothing higher. These bulb systems burn at 3000-3500K (Kelvin) while normal room fluorescent lighting start at 4000 up to 6500K. (see FIG. 11) This is the key reason doctors have been forced to work with the lights dimmed and the key reason projectors have lead to inconsistent diagnosis when being tested, as this is not what we call "Real World Testing".

The second reason—there are problems with projection systems because they are built with a major flaw in their design in regarding the distance a 1" image has to be projected. (See FIG. 22) On average this 1" slide image has to be projected some 13.5-20 ft for visual acuity testing. The resulting flaw is that these letters, when designed to be in scale on that slide, appear fuzzy when projected at the required distance. The diffusion of the light waves with this projected light refraction will always creates fuzzy letters. In a resent test it was discovered that letters projected even at 10 ft also appeared fuzzy on the silver-oxide screen—even when a person stood as close as 2 ft away from the screen. This creates a new problem in regard to the loss of "1° (degree) of true resolution" as required in the Snellen visual acuity formula of 1862. The third reason—is deformed letters. Projection systems suffer from uneven illumination and non-symmetrical trapezoidal-shaped letters due to the angles projection systems are installed. The projector is placed 4-6 ft on either side the patient. This angle of attack distorts the shapes of the letters. It's not uncommon for some patients to report seeing fuzzy letters when being tested and a practice that many doctors have accepted because there's nothing better—until now. This is why there is no consistency in visual acuity testing from doctor to doctor. How would you feel knowing that your eyes were being tested with 60 year old ideas and technology. Every projector is different and there is are no regulation or governing laws concerning the accuracy and measurement in visual acuity letters on "certified" projectors, there is only the formula that many companies and doctors have taken for granted at the consumers expense. The consumer is not getting the best eye exam possible and many may have overpowered glasses or contacts because of the old technology. As stated, all projection systems are inherently flawed and will not display a clinically accurate acuity letter with a 1° (degree) of true resolution that should be in the design of each letter for vision testing. This is not true for iQueVision testing system and the key reason for building the system. The iQueVision System will allow doctors to leave the lights on and produce a text book optotype with 1° (degree) of true resolution for each and letter with each and every test. LCD monitors burn a 400:1 or higher, almost double when compared to the silver-oxide screens of 250:1.

Using iQueVision A/VTS database program will create new testing procedures and a paradigm shift in the ideology, teaching and testing methods that are better than any other visual acuity testing systems to date. It should also be noted that with the resent development of plasma screens this has open door for iQueVision and a whole new way of thinking about vision testing for the future. The Plasma screen system will help in the design potential for "Real World Testing" under real lighting conditions. With contrast ratios of 3000:1, for better shadow detail and color depth.

INTRODUCTION—"DIGITAL FORMULA"

Under this patent I would also like to submit the discovery of this "Digital Acuity Vision Testing Formula" (DAVTF) as a minimum standard in visual acuity testing with computer testing systems. (See FIG. 8)

The digital minimum formula is: 400:1 Contrast Sensitivity@1° true rez visual acuity letters@min screen resolution of 1024×768>4500K ambient light.

While this formula sets a minimum standard for all digital visual testing systems it would certainly not preclude the use of any configurable built with a higher standard. Under these guide-lines any computer using a touch screen/touch pad or kiosk system with this digital formula for the purpose of visual acuity testing would be in violation of this patent. Anyone thinking that their formula is better would be in direct violation of minimum standard set in this patented when using the "DAVTF".

Example: the system we are currently testing exceeds the minimum formula and reads:

700:1CS@1° true rez@1280×1024>6500K ambient light!

(700:1 Contrast Sensitivity with 1° true rez visual acuity letters@min. screen resolution of 1280×1024 with 6500K ambient light.)

Note: High contrast, contrast sensitivity or contrast ratio does not mean brightness. High contrast is the measurement of gray scale or degrees of shade with the reference point of difference being the brightest white in relation to the darkest black on any given monitor. The higher the contrast sensitivity ads in the levels of gray scale detail that can been seen on the monitor. This contrast sensitivity translates into a better display monitor for viewing color testing when using 256 shades of color for each channel every monitor displays—Red, Blue & Green or (RGB) and gray scale or shadow detail. Also the 1° degree of true resolution is measurement in the distance between the white and black areas that define the spacing of each letter for each size used in any given test for each size of the letter used in the acuity testing. None of the slide projection systems on the market today offer a clinically accurate 1° of true resolution used as defined in the original 20/20 formula of 1862 by Dr. Snellen for testing visual acuity. In fact the small the letter the less detail the projected letter has. Fuzzy letters and a great lose in that 1° of resolution.)

The iQueVision A/VTS will also provide doctors with a first in animated eye testing procedures in a format that is better than any paper or slide chart systems in use today. For example, the letters of each animated chart can fade in and out as needed for each test procedure; letters can be moved across the screen at different speeds to test eye movement; color patterns can be generated for a detailed analysis of color blindness on impaired color vision; hue, density, saturation, and gray scale testing can all be built using an animation process to assist doctors in obtaining a better overall analysis of the patient's current eye or vision limitations. The system will also allow three-dimensional prospective with or without the use of colored red and green or polarized glasses using a 3D monitor LCD or Plasma screen. This system takes advantage of making it easy to access and use new technology as part of the continued development in visual acuity systems. It utilizes a pre-programmed database on any computer/Tablet PC/laptop/Unix computer server. It is controlled by an active matrix touch screen (kiosk), electronic personal data assistance (PDA) and or keyboard/mouse remotely or wirelessly linked to high resolution monitors, TV systems, plasma screens and or the new 3D monitor systems. Not only will all of the tests be incorporated onto pre-programmed database computer or Unix server, but it will also be designed to provide doctors with instant access to information on general eye care—helping their patients become more aware of problems by using the visual ads and information designed into the vision testing package.

One of the newest tests developed because of the iQueVision A/VTS is the "Dynamic Letter" Test. (As listed among the tests on FIG. 18) This letter or set of letters is a scalable letter controlled by the doctor. Just by holding a slider the doctor can scale a letter up until the patient can tell the doctor what that letter is. A numerical read-out displays at what point the patient can see the letter. From 20/10 all the way to 20/200 in 1 degree increments the doctor can take an exact reading and log them in to the patients records as a new measurement testing tool. As a new claim—no other projector can duplicate the Dynamic Letter test.

SUMMARY

Imagine for a moment your last eye examination . . . the doctor had you look at a projected slide on a gray or silver flat surface some twenty feet away and toggled through various static letters as a testing systems. The doctor dimmed the lights and told you to look at this dimly lit screen illuminated by a single projector. So there you are in the dark trying to focus on this letters some 20 ft away and the letters are fuzzy. Suddenly the doctor can't find the special test he or she needs and begins to takes you from room looking for that one test. The doctor may have even taken you to a special room for color or 3D specialized computer testing. Another obvious problem is the 20 feet of office space required for performing an eye examination adding to the cost of overhead.

Now, imagine being in a room half as long, looking at high resolution, high contrast flat screen 17-20" monitor or a 32-72" inch Plasma Screen (depending on the configuration purchased) and taking a new animated eye test=interactive and fun=viewing an educational slide show, educational video and even an instructional slide show or instructional video about your particular problem or procedure, all from that same monitor. As the doctor touches the active screen linked to a computer the passive screen, at the other end of the room, changes and displays different tests.

Each time the doctor uses the touch screen active monitor a new and different test is shown. With the iQueVision: A/VTS, the distance factor can be simulated on a monitor or TV screen. Using the right monitor with the pre-configured computer system, the testing room would only require half distance in size, 10 feet. Now image a plasma screen being used to project real world images, a street with trees and houses. As the test proceeds you're asked if you can see the various signs posted to simulate different views—not realizing that your also being tested with visual acuity letters on each sign at different points and sizes along that street. This system would help not only in the initial testing phase but would also help in the prescription phase during a follow up where the patient should be re-tested with their prescription glasses on. This system would also replace computerized auto refractors. These machines measure the light refraction automatically in order to find the right prescription, however the same auto-refractor can't be used when wearing the prescribed glasses. The plasma screen system would add in the follow-up exam to ensure the lenses were correct in "Real World Vision Testing". Plasma screen testing has never been used—by anyone.

The iQueVision: A/VTS would include animated tests and slide test with letters, numbers, pictures in 2D and 3D, symbols, graphs, charts, color testing, gray density, depth perception, 2D and 3D animation, hue and density. (See FIG. 18) On the same a pre-programmed computer system, doctors who purchased the system, would have access via the Internet using browser technology such as Netscape, Internet Explorer, Safari or any other web browsing tool to download the latest up dates and new animated computer testing methods, (see FIG. 15) if and when the doctor wants to purchase another test. (see FIG. 5) At the core of iQueVision system a software tech with an internet connection to the server itself can quickly be accessed for on sight trouble shooting before sending in a hardware tech to fix the problem. Using a portable laptop computer or Tablet PC, the same testing system is design for 10 ft or 40 cm testing in off-site or remote locations. The general scope of using this new iQueVision: A/VTS is endless in order to achieve better testing results with all of the primary tests this system can offer technically accurate, more consistent results and surpasses any other projection based technology in use today.

Research indicates that nothing else like the iQueVision: Animated/Vision Testing System exists for testing visual acuity today. The new "Digital Formula" (see FIG. 8) raises the bar and sets a new standard for displaying, animated vision tests, slide tests and visual acuity letters. When it is viewed on any high resolution TV, computer monitor screen, laptop, tablet pc or plasma screen this system allows for greater flexibility, portability with wired or wireless ease of use. (See FIG. 19A) This system will improve with new technology to help keep testing procedures current for every doctor who purchases the system but will always remain a kiosk, touchscreen, keyboard/mouse or voice recognition driven system.

DESCRIPTION

The level of difficulty in designing a system such as this far exceeds the capabilities of most computer users. A thorough knowledge of Unix operating systems and many software programs and the ability to integrate the use of the programs to produce the final product is required. Creation of this Animated/Vision Testing System involved the use and integration of the following programs.

1. Adobe Photoshop
2. Adobe LiveMotion
3. Adobe Illustrator
4. SketchUp
5. Adobe GoLive (HTML, XML)
6. Adobe Dimensions
7. Adobe AfterEffects
8. Apple iMovie
9. FinalCut Pro
10. iDVD
11. DVD Studio Pro
12. Maya or similar 3D software
13. Unix Operating systems and Unix programing software
14. FileMaker Pro (the database)
15. Macromedia's Flash
16. Macromedia's Fireworks
17. Macromedia's Dreamweaver Other technologies include: Apple Computer's QuickTime technology for the conversion process. The equipment required includes the iQueVision: A/VTS software, a Computer/Tablet PC/Laptop/Unix based Computer Server (consumer, portable, or other computer-related product), a hi-definition television, computer monitor or plasma screen. The system can be modified to the size of the screen required in order to properly administrator a visual acuity test using the iQueVision: A/VTS. The technology will also follow for the use of royalty-free video, photos and or venders commercial products as may be requested by a doctor to produce a customized version of the iQueVision: Animated/Vision Testing System using any of the touch screen (kiosk) computer, Tablet PC, PDA and or Keyboard/Mouse input devices. This system would also include a web browsing interface to access the internet for product or research, information or patient information. This system would also include an optional wired or wireless keyboard/mouse and/or a wired or wireless monitor/plasma integrated system as an up grade. All of these features combined in a cross platform operation with internet access from an examination room using the iQueVision: Animated/Vision Testing System can not be found in any other vision testing system to date.

SCIENCE

Each animated/slide letter is based on a mathematical formula for 20/20 visual acuity testing established in 1862 by Dr. Hermann Snellen. (See FIG. 8) As previously stated the "Digital Acuity Visual Testing Formula" or "Digital Minimums" is the key to making this paradigm shift in science work. It takes Dr. Snellen formula from 1862 and modifies/updates it using 21st century technology. Other testing modules include, but are not limited to, the following: color—density—dot—2D and 3D art animation, all designed to work seemlessly on the iQueVision A/VTS. (See FIG. 18) Once all the tests are approved in design and functionality by clinical trials, the system will be marketed to doctors and/or their patients for treatment and therapy. As mentioned other uses include a home based therapy system that doctors can either sell or give to patients who have internet access to improve their vision with home testing and therapy sessions. The process for designing a new iQueVision: A/VTS is complex, but the end result is a system that any doctor can use and every patient benefits with a standardized testing system that replaces out dated systems.

While most testing system are restricted to one platform or operating system, iQueVision: A/VTS is not. As mentioned in the title of the this patent the programs used to build this vision testing system will work on not just one but three different platforms. (See FIG. 12) This programed (database) is designed to work on the three operating systems Macintosh/Unix, Windows and Linux. This versatility of being the only cross-platform system distinguishes the iQueVision A/VTS as a very unique, one of a kind vision testing programs among the stand-alone systems currently on the market today. This is the core attraction to operating the iQueVision Testing system and another feature that no other system can claim. The entire testing program can be ported or used with your favorite operating system or one that may already has in place. The materials used to make the iQueVision: A/VTS product include all formats of computer based systems, touch screen technology, keyboard, mouse, tablet PC, PDA or even voice control.

FIG. 1: Shows the Standard Alone Configuration of the iQueVision: Animated/Vision Testing System, the design to use with computer/Unix based computer server via remote control with a touch screen (kiosk), PDA and or Keyboard with a Hi-resolution monitor or TV screen in a clinic.

FIG. 2: Shows Multiple Operating Systems on a Unix Server iQueVision: Animated/Vision Testing System with a computer/touch screen (kiosk), PDA and or Keyboard with an internet connection and Hi-resolution monitor or TV screen. This is also the cross-platform configuration showing the Macintosh/Unix, Windows and Linux platforms.

FIG. 3. Shows the Multiple OS with the total number of uses and host files that can be accessed using the iQueVision: Animated/Vision Testing System with a portable laptop 17" computer and or Hi-resolution monitor or TV screen with wireless or hard-line internet connection.

FIG. 4. Shows the Portable or Wireless Connections to a Unix Server iQueVision: Animated/Vision Testing System on both touch screen computers and monitors.

FIG. 5. Shows the iQueVision: Animated/Vision Testing System with home therapy application for vision care with a computer connection via the internet on different browsers.

FIG. 6. Show the subcategories listed for different configurations and uses, but is not limited to these specific fields of vision care.

FIG. 7. Shows the iQueVision: Animated/Vision Testing System functionality and menu control. Along with a list of categories that can be added to the system as it's being developed.

FIG. 8. Shows the Measurement Formula for 20/20 Vision as it has been used over the past 60 years in the development of projection systems. However, it also shows the new Digital Acuity Vision Testing Formula (DAVTF) that was discovered during the building of the iQueVision: Animated/Vision Testing System.

Figure 9B:
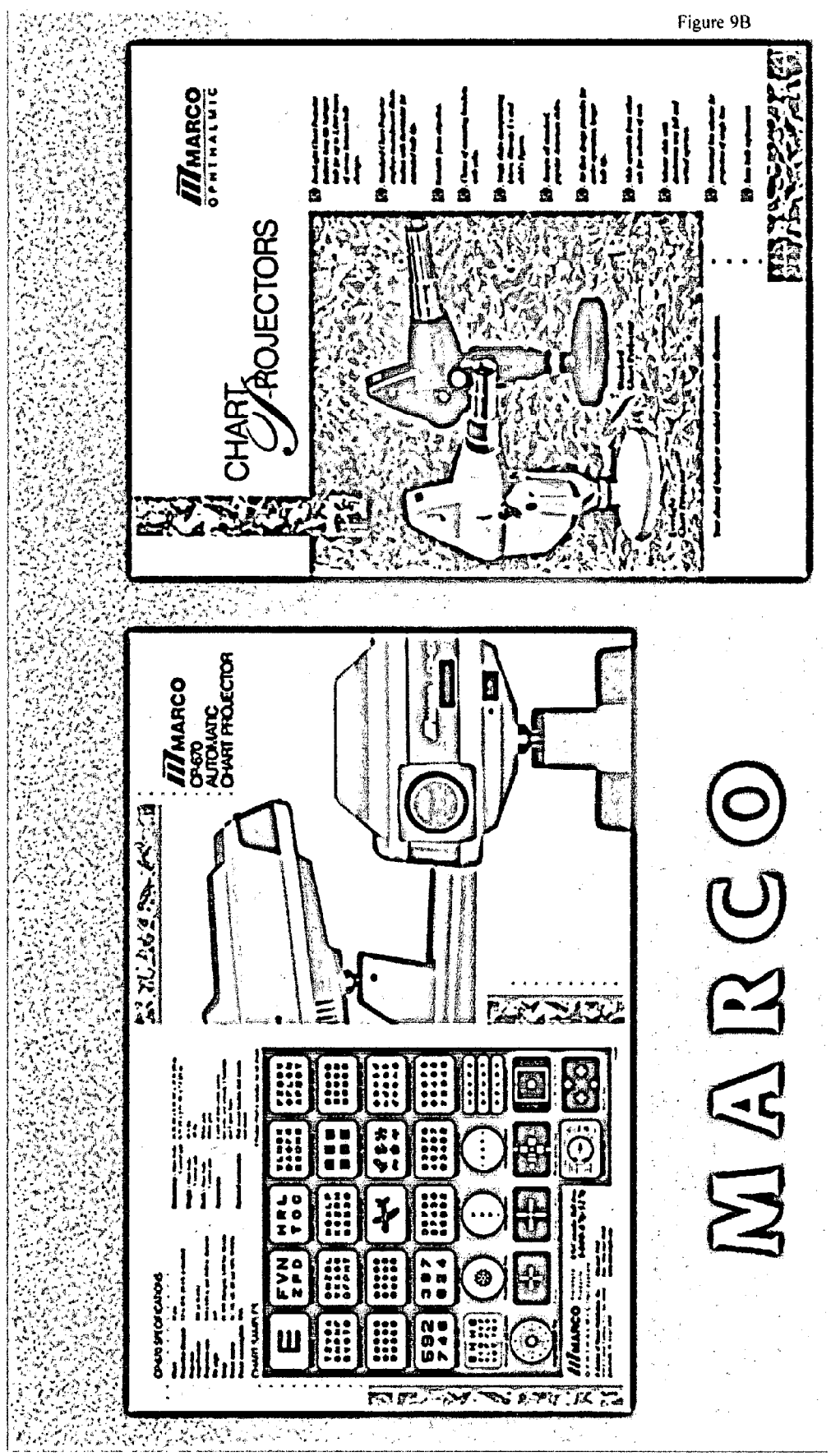
Figure 10:
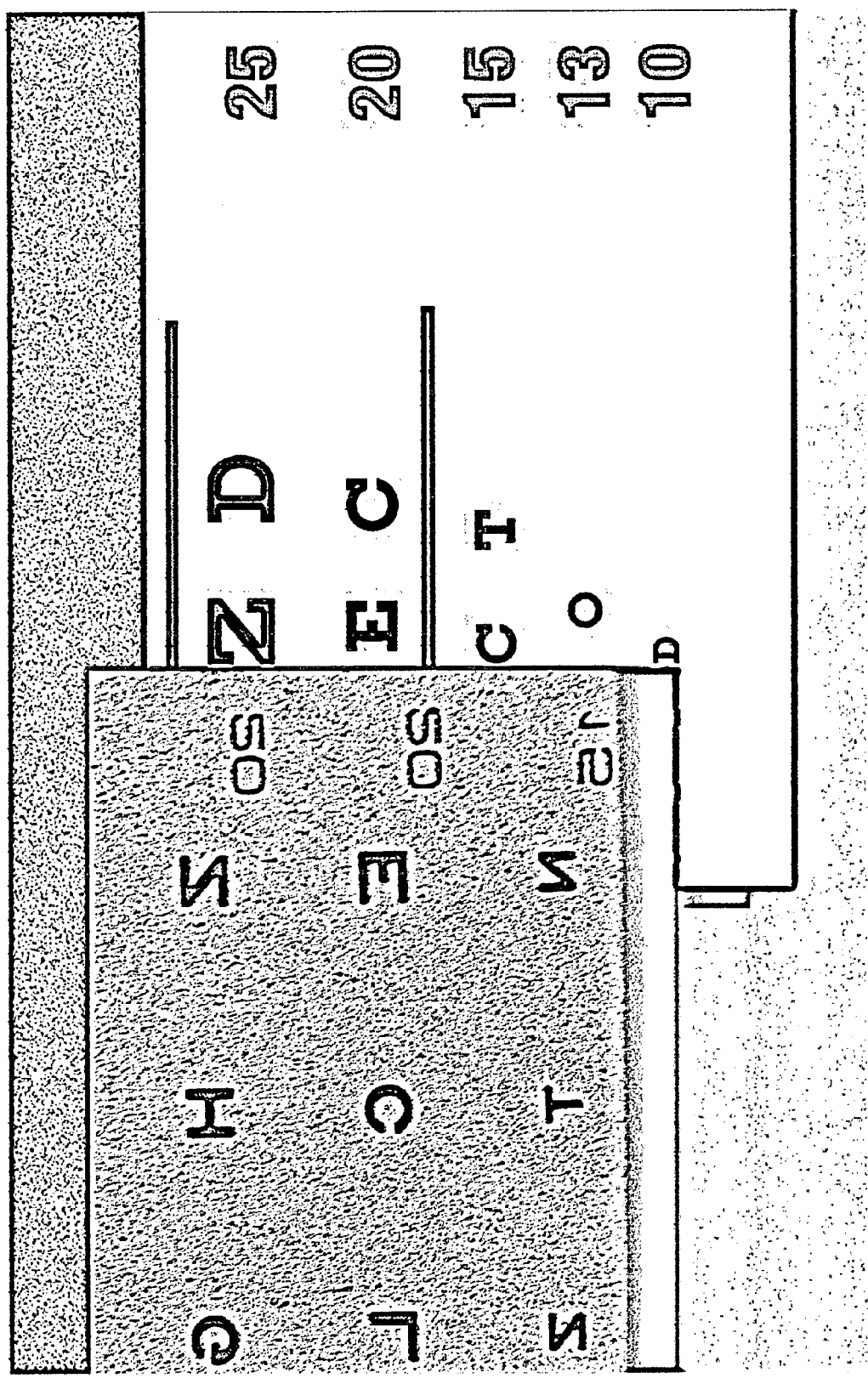

FIGS. 9A, 9B, 9C, show the three top competitors in this field and the projection systems they currently sell, FIG. 10. Show a sample image of the what the current projection system (on the left) are providing as compared to the quality of the same size letter (E@20/20) the new iQueVision Test (on the right) can produce.

FIG. 11. In the course of study general "Observations" came to light with regard to Bulb life, Room Lighting, and the Slides used in testing. I have also included an image of the first slide projector patented in 1922.

Figure 12:
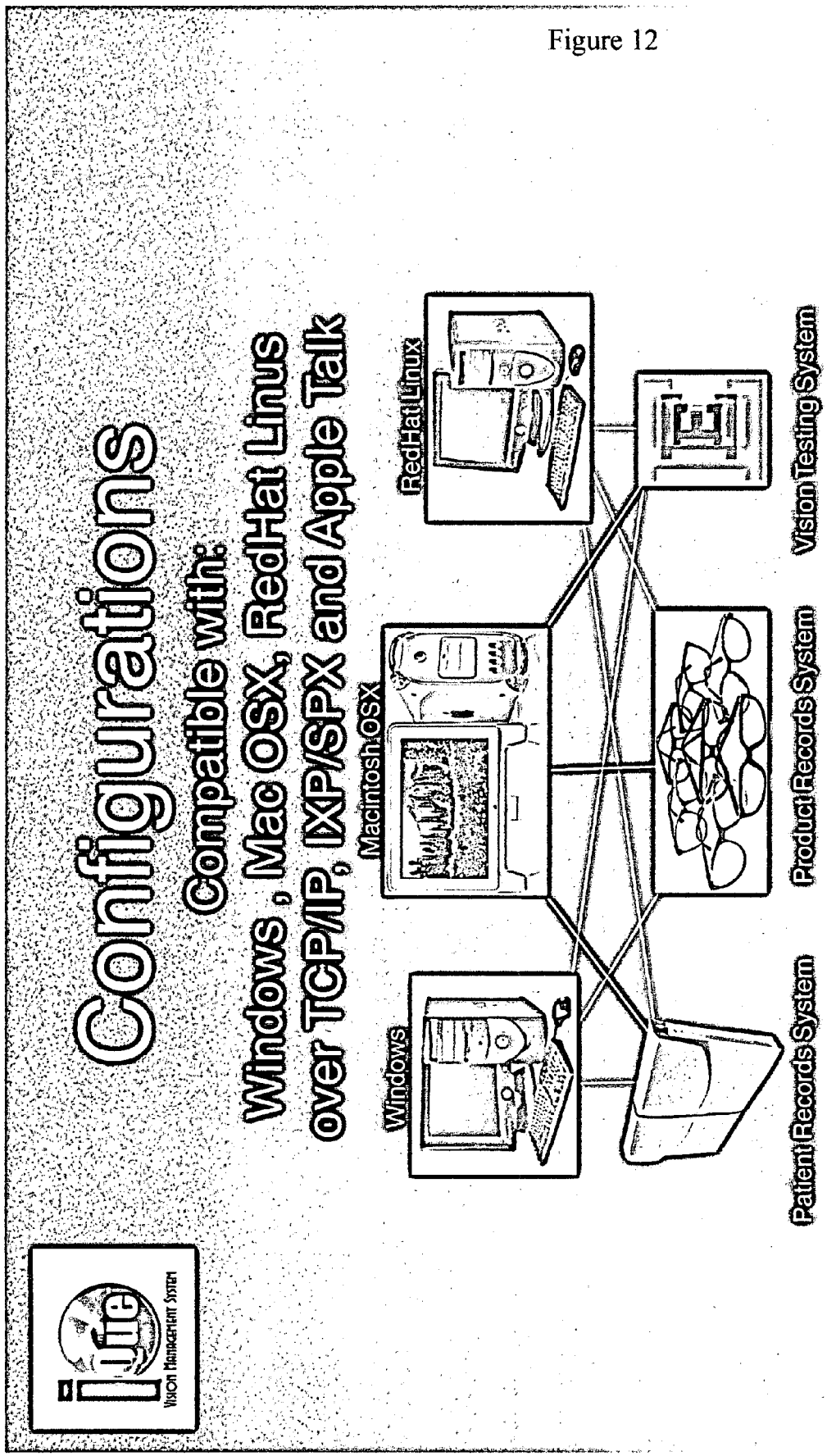

FIG. 12. Shows the iQueVision A/VTS cross-platform configurations showing the same vision testing system can be accessed by all three operating systems.

Figure 13:
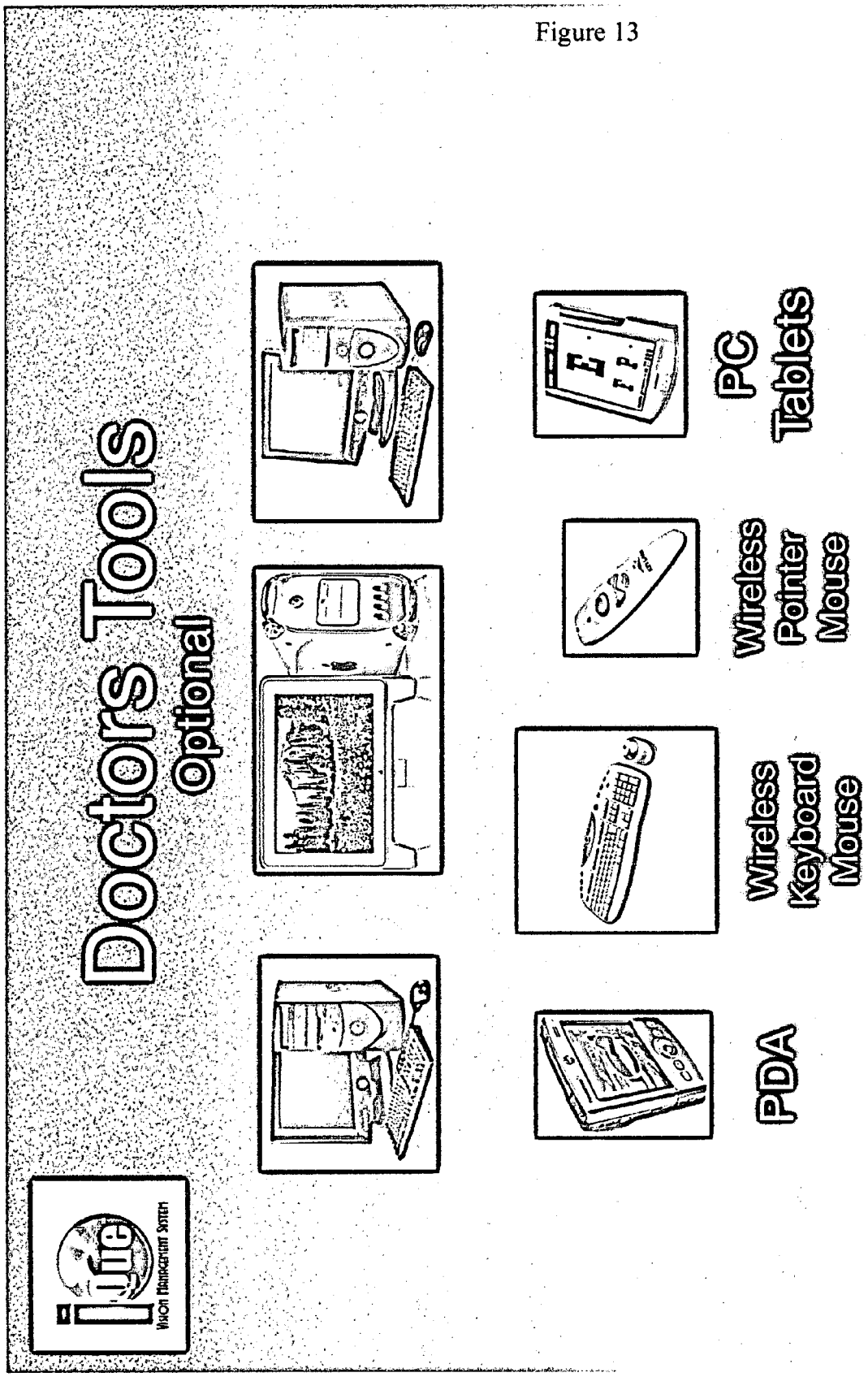

FIG. 13. Shows the number of Optional Tools available to the doctor in order to use the same iQueVision A/VTS.

Figure 14:
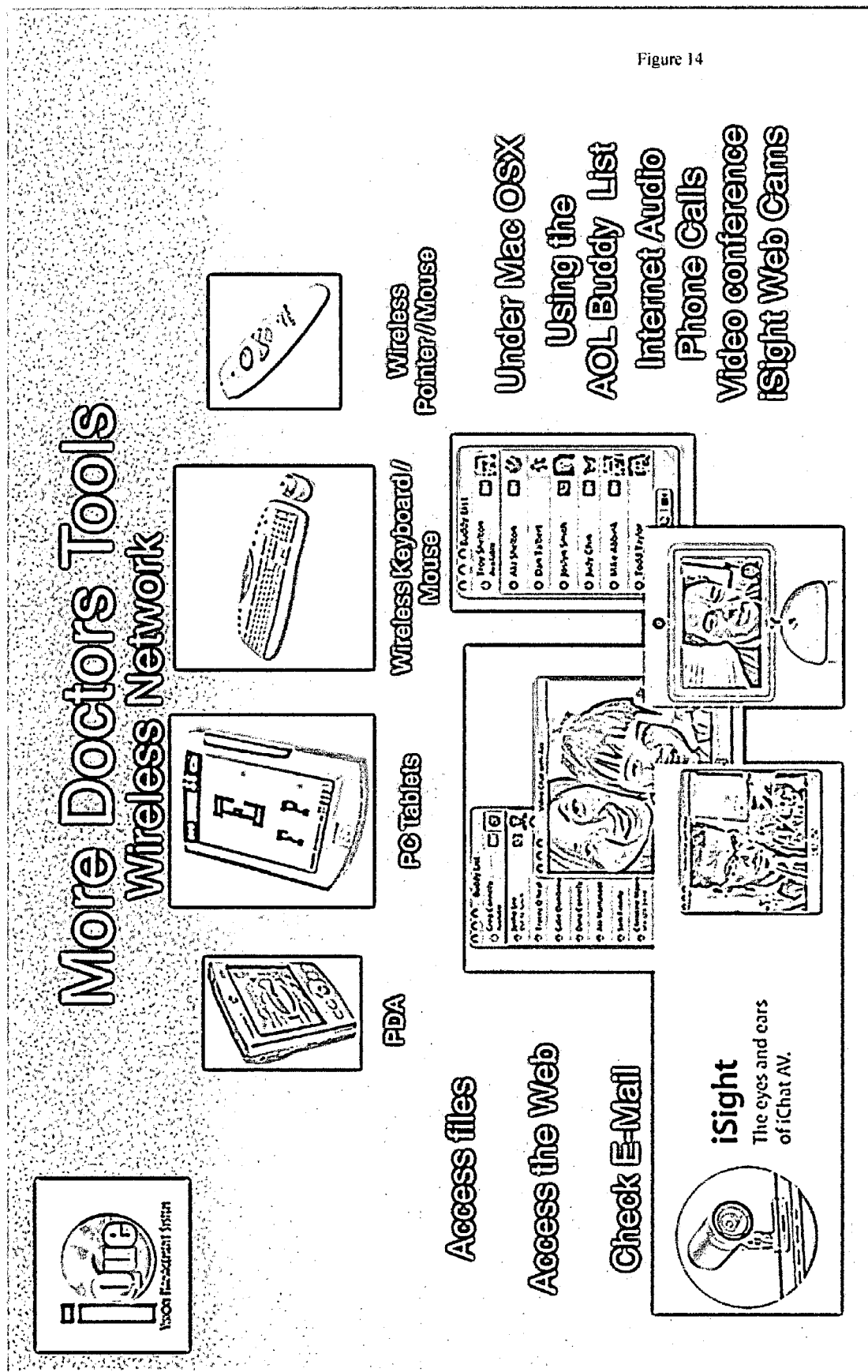

FIG. 14. Not only does the doctor has a choice of tools but also the choice of options that can be added as needed or upgraded to the iQueVision Testing System.

Figure 15:
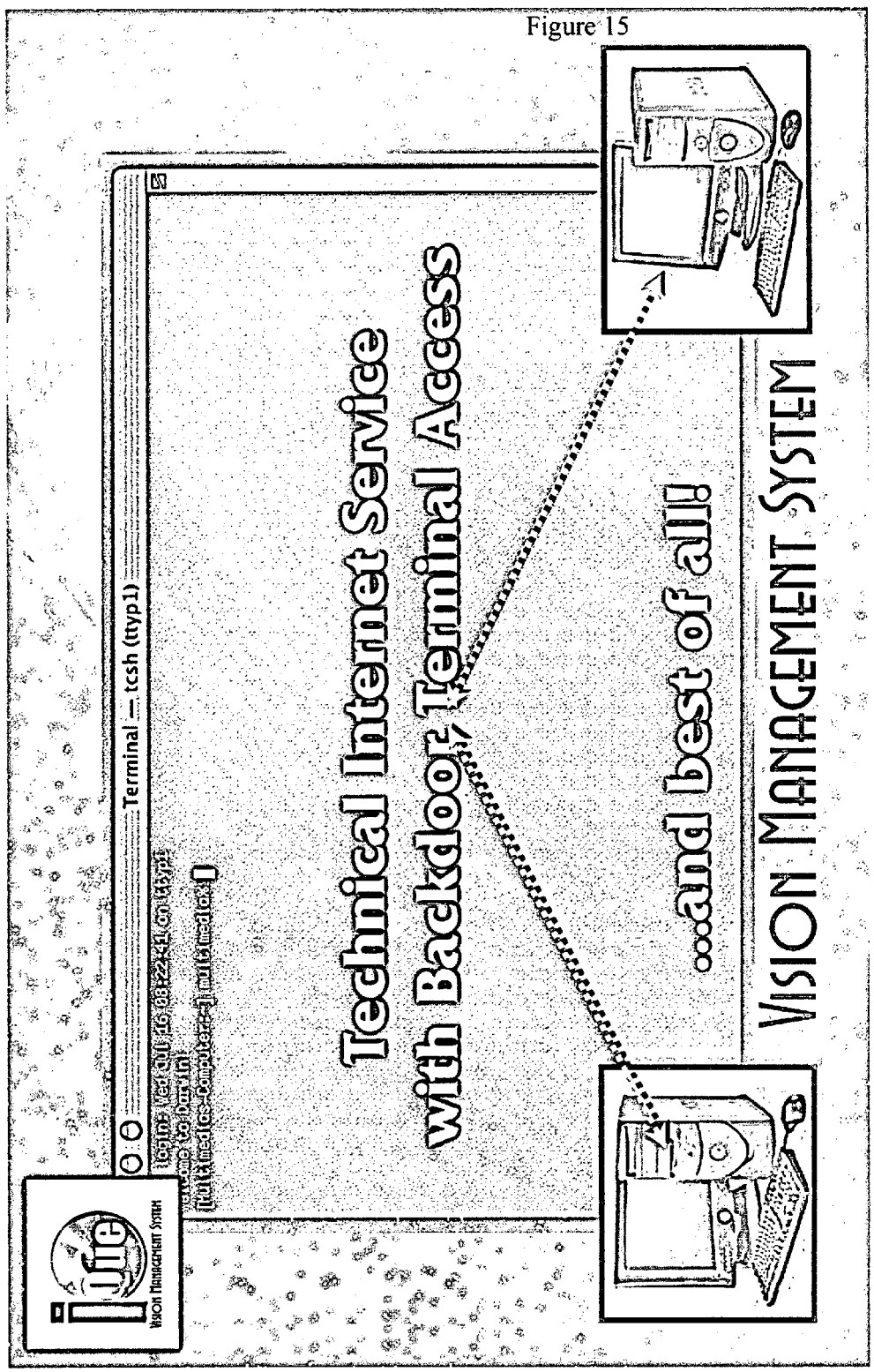

FIG. 15. Shows the "Backdoor" terminal connection iQueVision would have in servicing and maintaining each unix server sold to a clinic. Using a command line system an tech can literally access the system, fix the problem and restart the system via a simple internet connection.

Figure 16A:
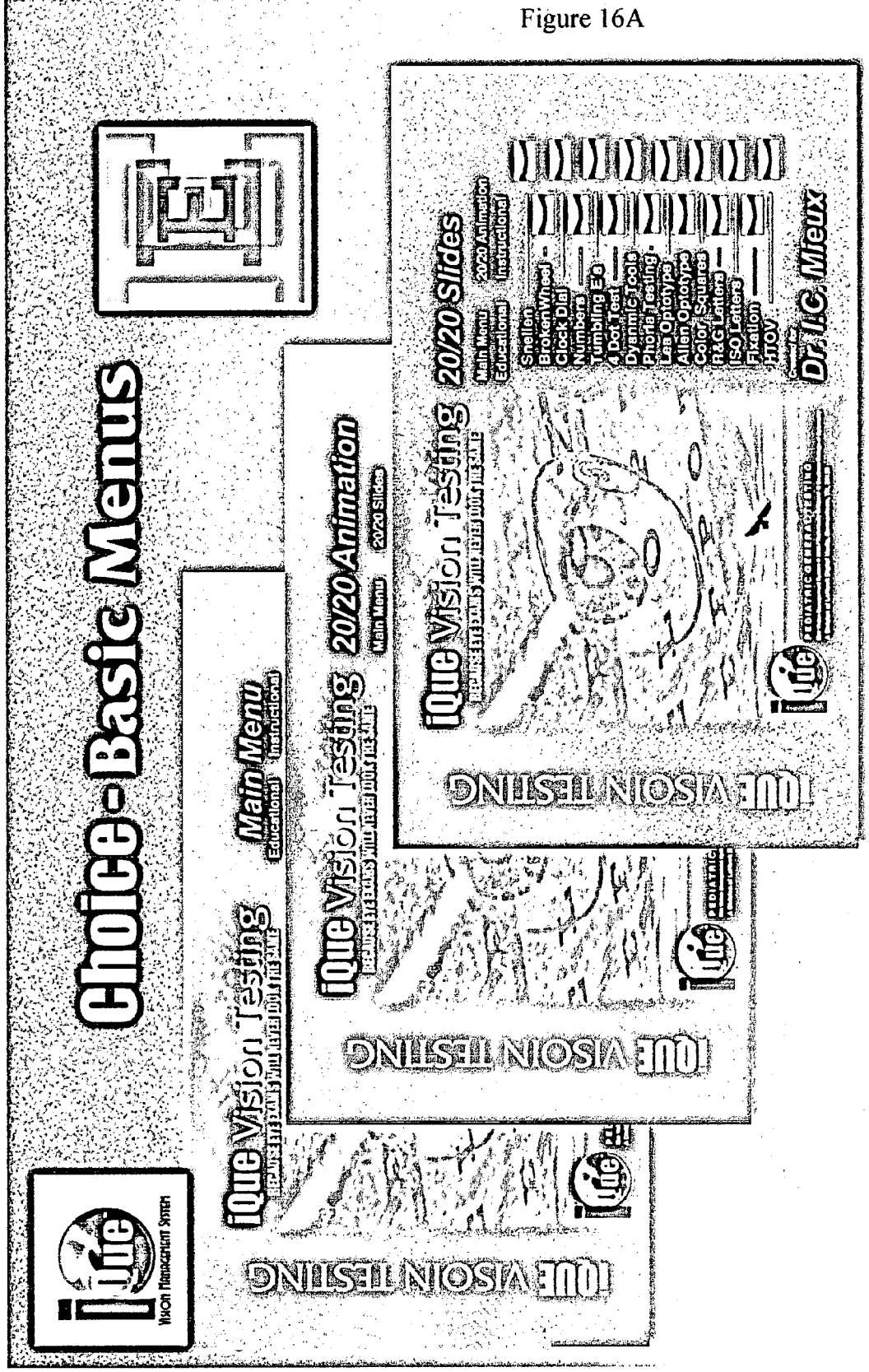
Figure 16B:
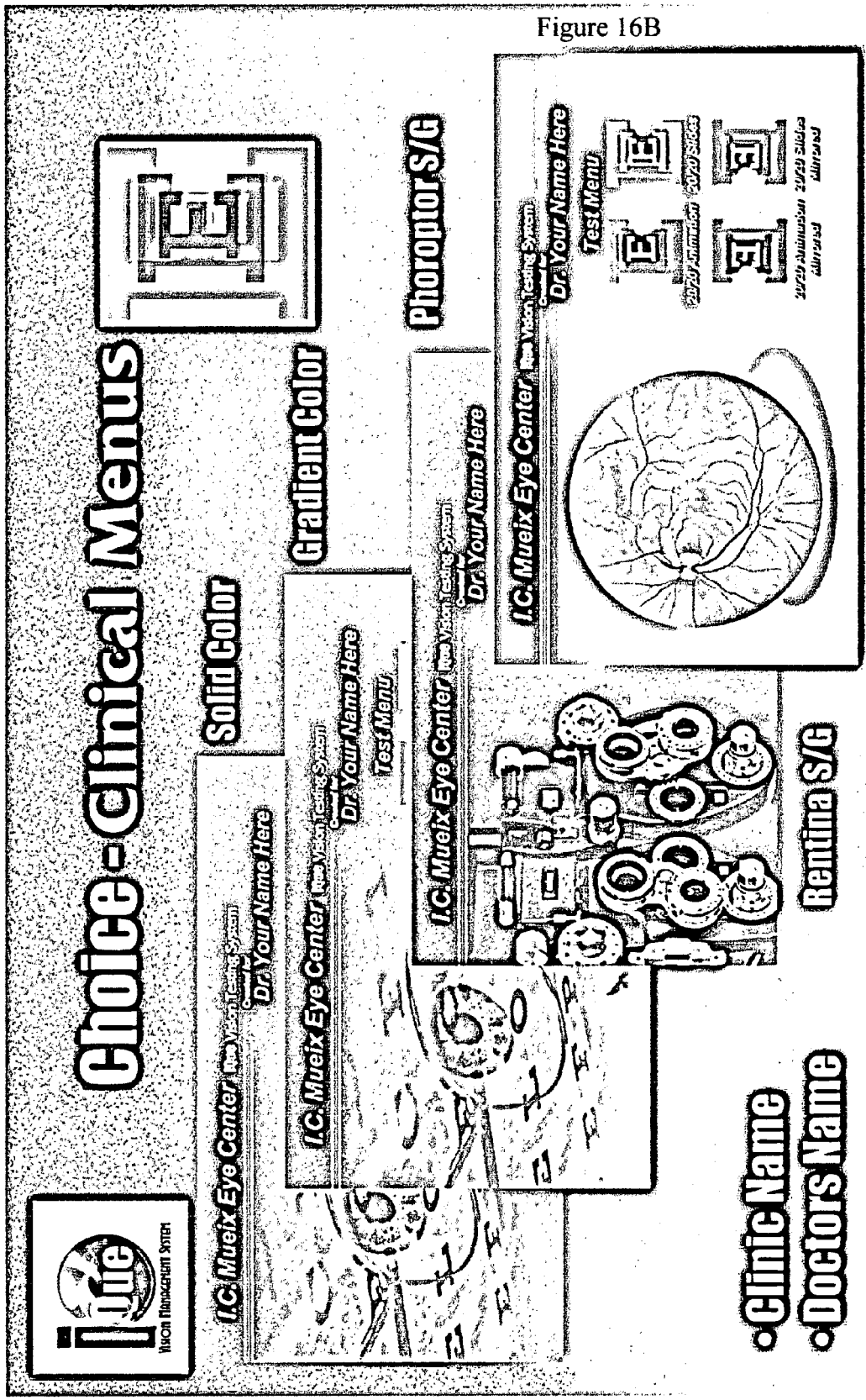
Figure 16C:
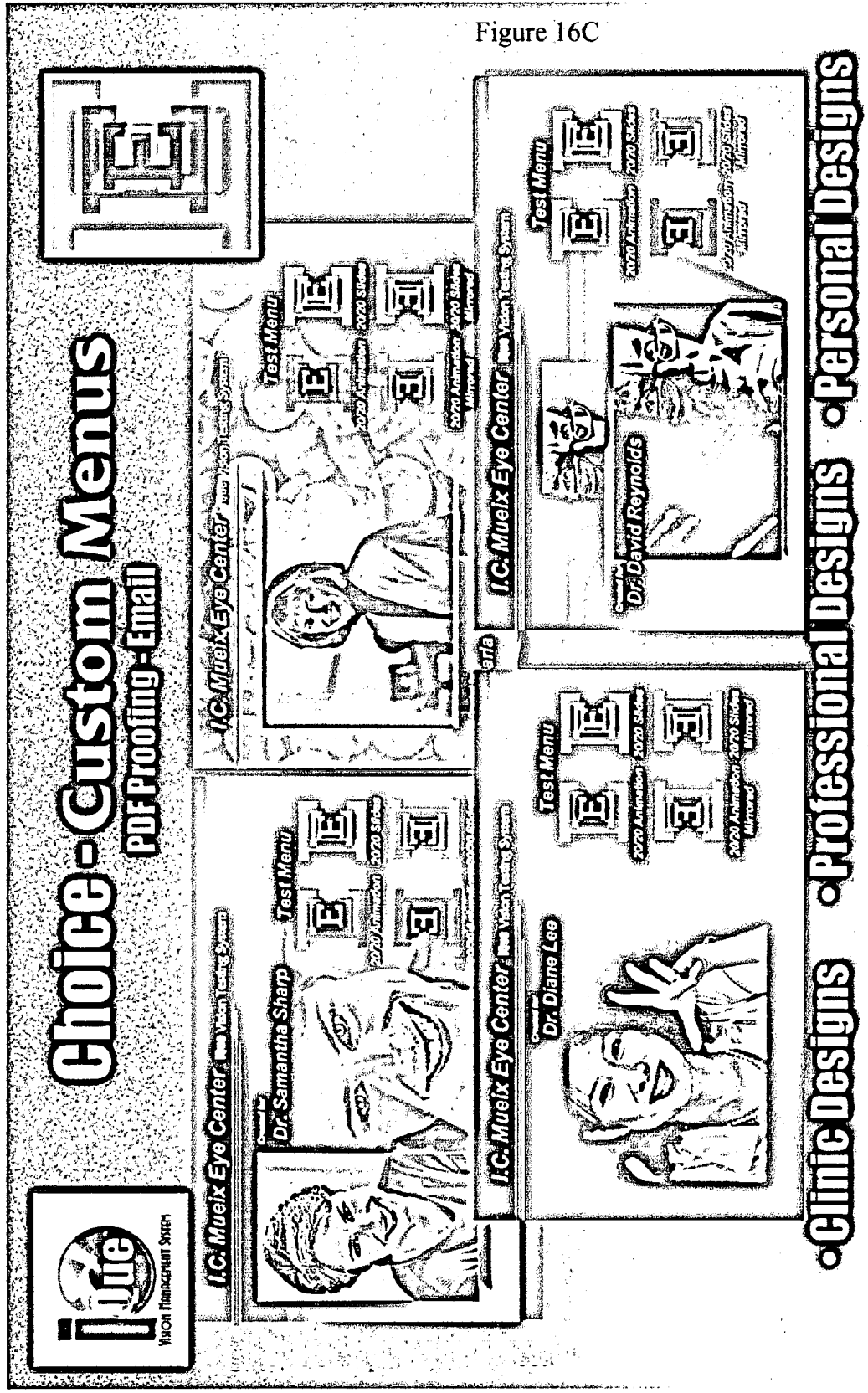

FIGS. 16A, 16B, 16C. The next three sections show the choices that are available to the doctors who purchase this system. 16A—Basic Menus, 16B—Clinical Menus and 16C—Custom Menus. This is also unique to iQueVision Testing System as it leads the way in personalization for each and every doctor or clinic.

Figure 17:
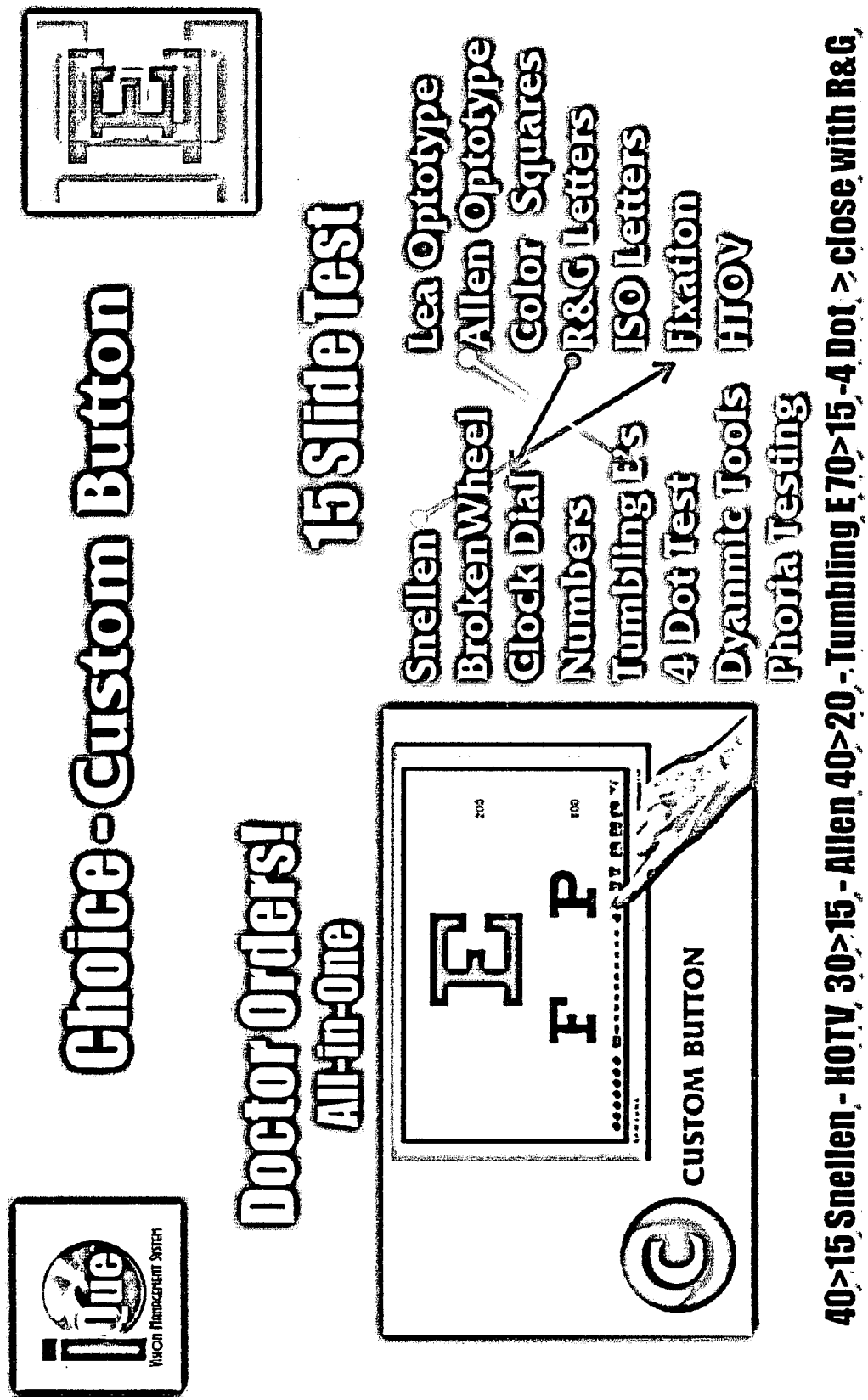

FIG. 17, A custom button can also be added to the menu system for each doctor. Each doctor has his or her own operating method. Using the custom button organizes the test in the pre programmed order in which the doctor would like to use them. This is a time saving functions as all the entire testing process flows from one test to another without having to return to the main menu.

Figure 18:
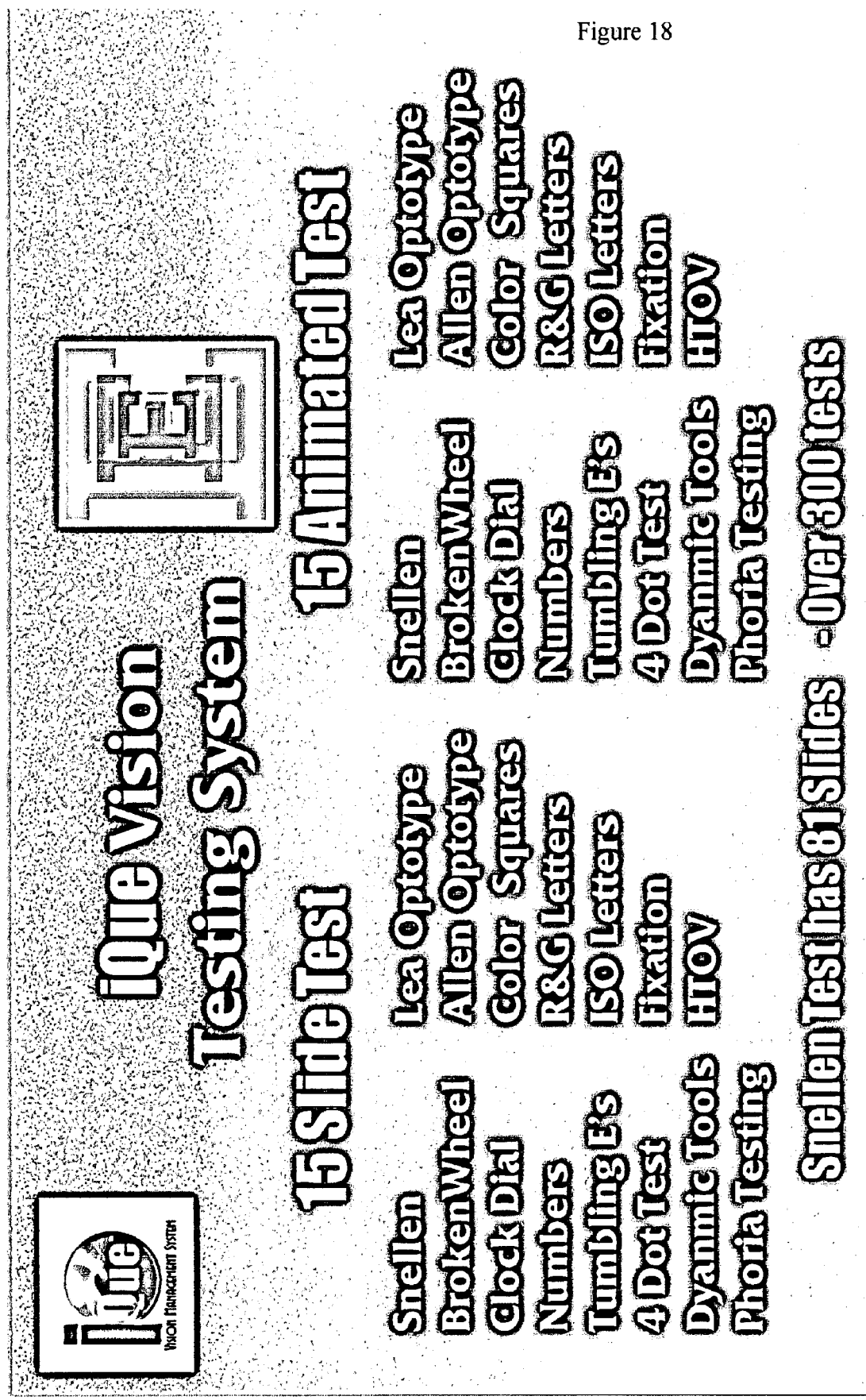

FIG. 18, Show a list of the top 15 test that can be accessed by the doctor in both Slide and Animated form. You average slide projector can only handle 30 test. The new Snellen Test alone has 81 slides which is more than double then the current test. Bring the total number of slides to over 300.

FIGS. 19A, 19B, 19C, 19D, 19E. These are the collective configuration 19A. "Stand Alone" Mac/Unix. 19B, "Stand Alone" PC Configuration. 19C, "Cross Platform with Server Connection". 19D, Portable Systems" and 19E, "Server Combinations" In the "Stand Alone" configuration this show another important aspect of this system in having a choice between DVI and VGA. DVI simple put is an extension of this the same screen, where VGA, if you look carefully, is a mirrored image of the same picture on both screens. This will be come more clear with FIGS. 20A and 20B.

Figure 20A:
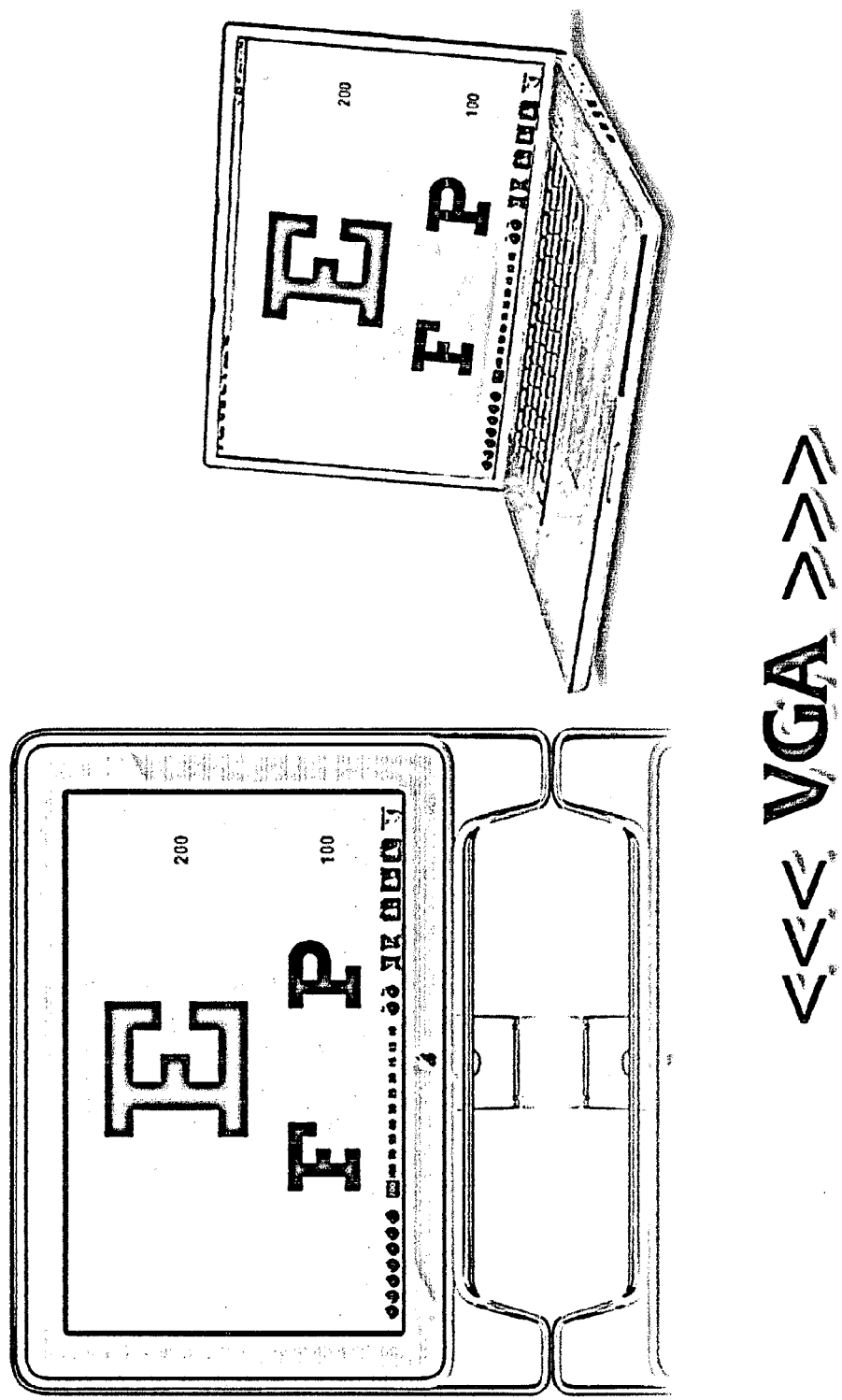
Figure 20B:
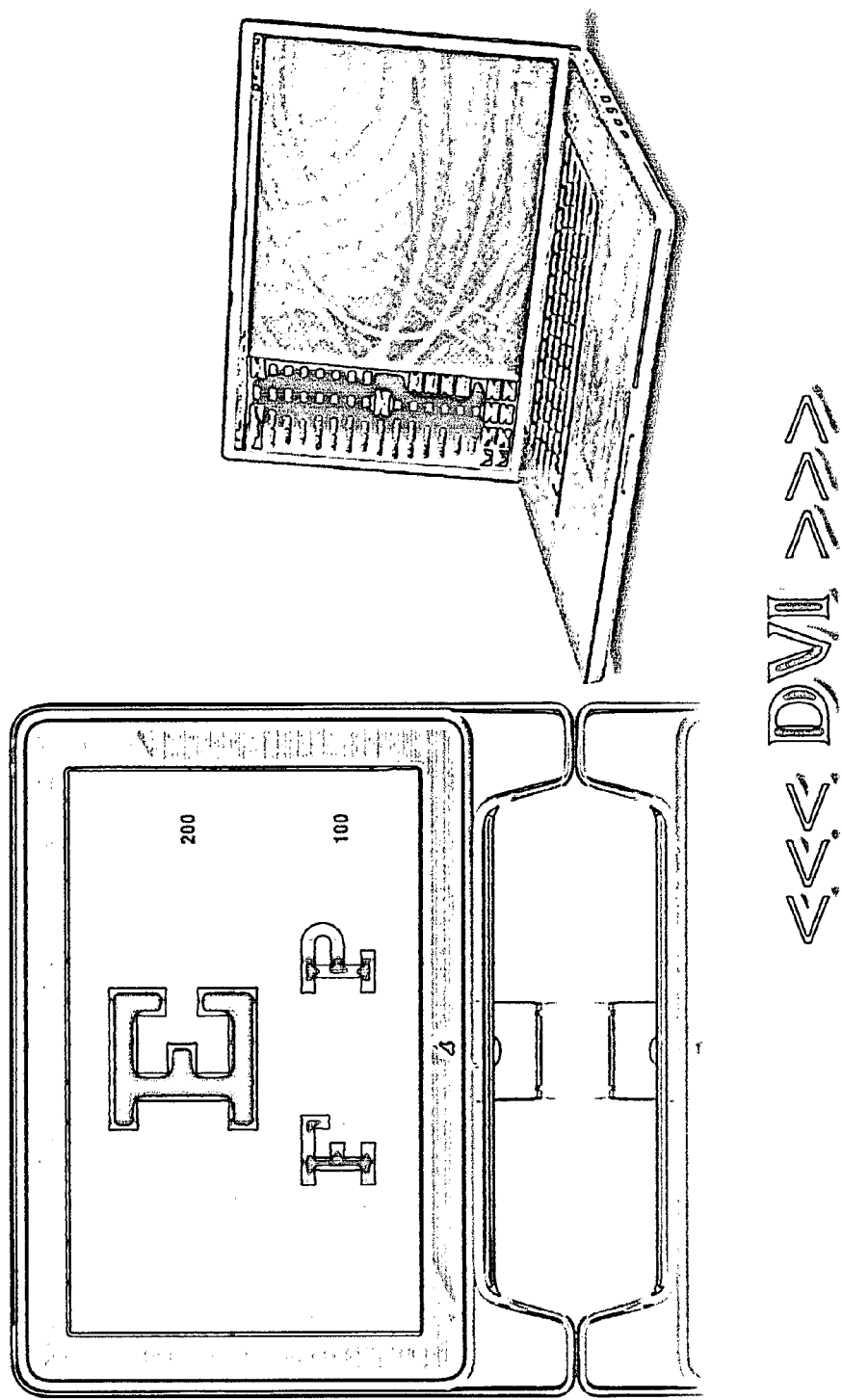

FIGS. 20A. & 20B. 20A—shows the mirrored connection or VGA connection between the active and passive monitor. Meaning that what the patient will be able to see the control panel at the bottom of the screen, even thought it will be too small to read at 20 ft. 20B.—of the two systems the DVI system is better as you can see the control panel only appears on the doctors portable laptop and the patients screen shows only the test that is displayed.

Figure 21B:
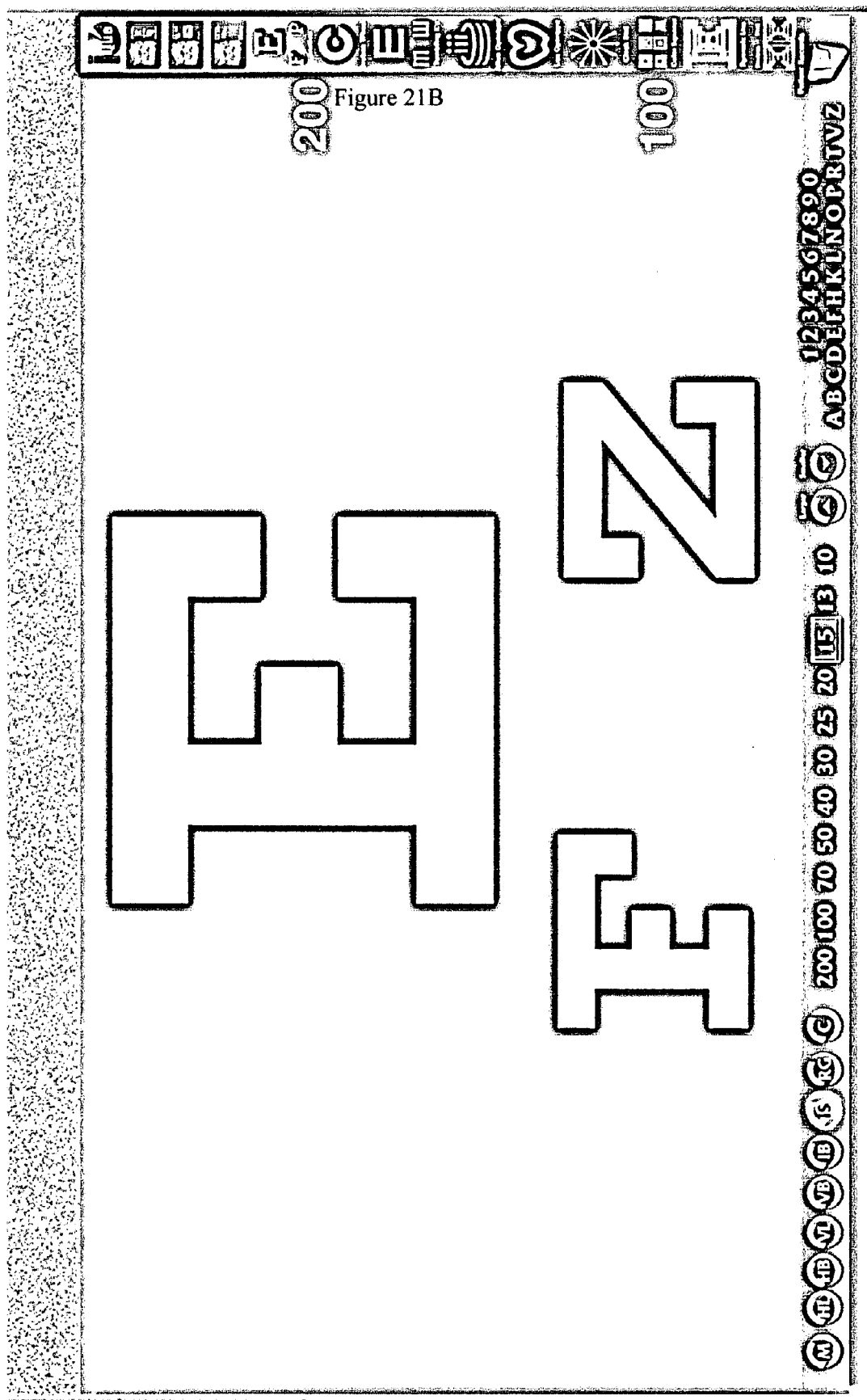
Figure 21C:
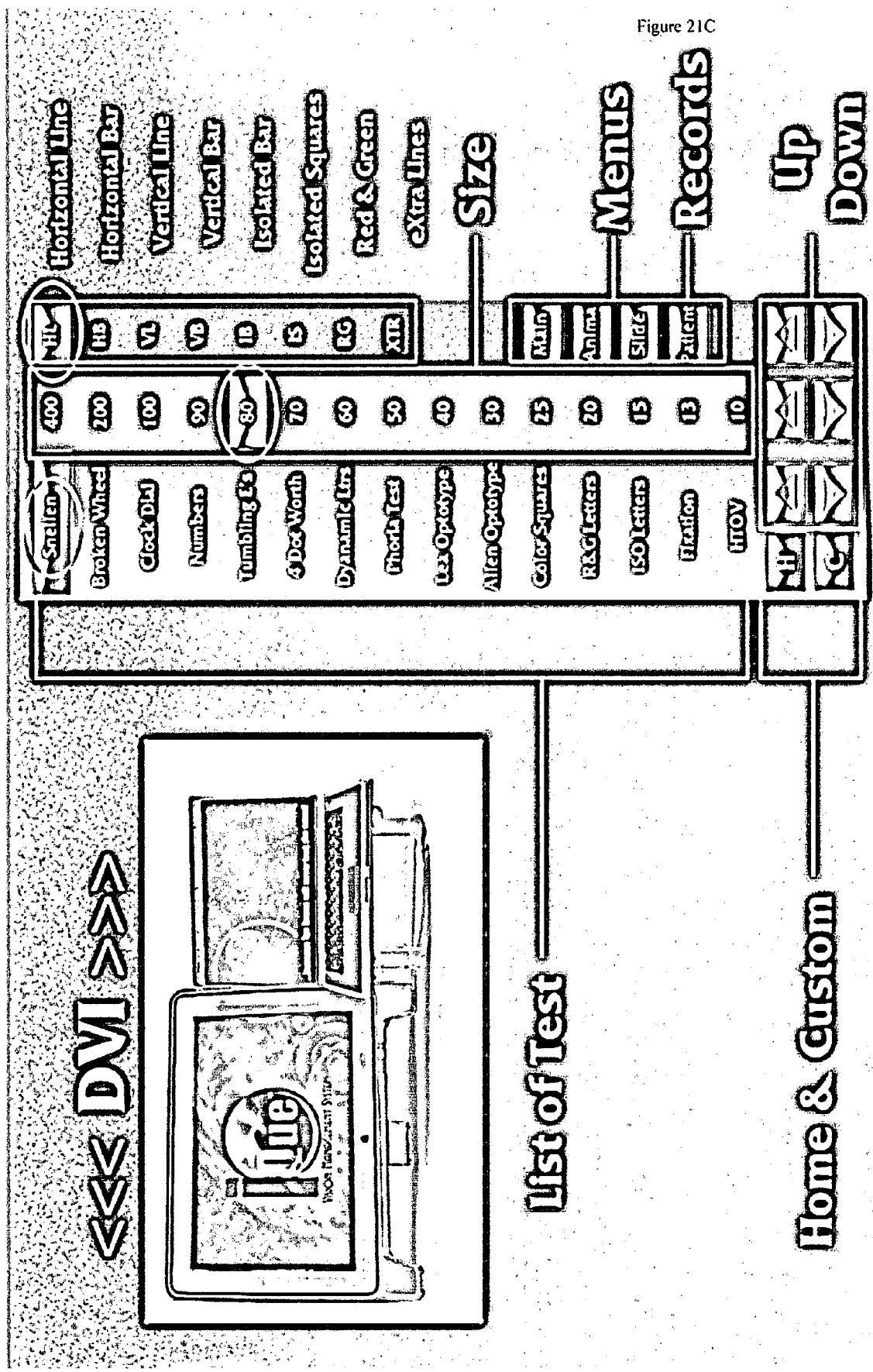

FIGS. 21A, 21B, & 21C. These represent a general idea of what the interface may look like when completed. Demos have already been made using the images from 21A. and 21B. 21C—is the newest addition to the menu system with a general idea of it's control function and features.

FIG. 22. This is where it all comes together, here you can visual see the different types of rooms currently being used by doctors today. The first two rooms show the angle of distortion from projection systems and the last room with iQueVision A/VTS direct, line of sight viewing on a bright monitor.

FIG. 23. This show Photo 1 and Photo 2. In Photo 1 you can see a slide projector in the dark trying to project an image 20 ft across the room. The is a great representation of the just how dim the letters are at the opposite end of the room and just how hard it is to read them. In Photo 2 the rooms lights have been turned on and yet using a large monitor screen you can easily read the letters on the test chart. This also show how a doctor using the touch screen system would be able to change or display any letter in any size or call up any other test needed during the examination process just by pushing the touch screen kiosk.

Example: The technical equipment could be, but is not limited to, a system such as the Apple Unix Server or Laptop, Tablet PC, PDA, a Planar 19" wide TTF LCD Flat Panel monitor, or the Actual Depth 15bx 3D LCD monitor. As long as the iQueVision A/VTS computer/laptop/Unix server, High resolution monitor and computer system are capable of providing the right control, specific resolution and contrast ratio while meeting the minimum requirements of the "Digital Minimums," the choice of hardware equipment is entirely up to the user.

OPERATION

In day to day operation, the iQueVision: A/VTS is accessed via a local area wired or wireless network to a computer/laptop/tablet pc/PDA/or Unix based computer server. (See FIG. 1)

1. Turning on any one of the system mentioned will activate a passive monitor at the other end of the room and directly opposite from the patient sitting in the exam chair. An active display monitor, used by the doctor, would display a control panel of animated/slide tests from his touch screen (kiosk), PDA or Keyboard/mouse located next to them. (See FIG. 23) Using the touch screen system the doctor would choose at test that is displayed on the passive monitor in front of the patient.

2. Using the touch screen (kiosk), PDA and or Keyboard/mouse along with the equipment listed above, the doctor would then pick one of the general test menus. Once the appropriate test category was located, the doctor would administer the animated/slide vision test. The doctor would have full control over each animated/slide test, being able to start, stop, reverse, pause and return to the main menu as desired at the touch of an on screen button.

3. Using the remote touch screen (kiosk), PDA and or keyboard/mouse each sub-menu category would give the doctor better options and single out the testing process he or she believes would assist in making the best diagnosis. Having "all" the test in one system either animated or in slide form speeds up the process and avoids the need to take the patient to another room looking for a tests. Using the iQueVision: A/VTS allows the doctor a freedom of choice, instant access, and operational ease of use.

4. Using the remote touch screen (kiosk), PDA and or Keyboard/mouse the doctor would also have access to education videos, charts, graphs or any teaching or training tool also design to be quickly access using this system.

5. Turning on the computer/laptop/tablet pc/Unix based server with the optional keyboard and internet access the doctor can quickly call up any reference material, product or training tool to help the doctor/patient relationship. This addition also allows the doctor to monitor and support a home therapy system given to the patient. The doctor would also be able to demonstration how to use, access and apply the home therapy system.

(Note: Custom interface—While the sample pages are designed to give better clarification, they are not intended to represent the only style that can be designed into this iQueVision: A/VTS. This architecture also lends itself to customizing for individual doctors who want to show their own company name or logo, style or preference in mind. While the general appearance of the menus in the computer may appear different according to a doctor's preference, the basic science and functionality that goes into creating this iQueVision: Animated—Vision Testing System will be the same on every computer/laptop/Unix based computer system with touch screen or keyboard/mouse.

The invention claimed is:

1. A device for performing in eye test, comprising:
    a display for animated visual acuity letters and scalable dynamic letters,
    a computer to control said display and to link to a patient database,
    said display having at least a contrast sensitivity of 400:1, a true rez visual acuity letter of 1°, a screen resolution of 1024 and a ambient light 768>4500K.

2. A device for performing in eye test as in claim 1, wherein said device includes a slider to control the scalable letters by 1° increments.

3. A device for performing in eye test as in claim 1, wherein said animated letters can move across the screen at varying speeds.

4. A device for performing in eye test as in claim 1, wherein said display includes a color pattern to test color blindness.

5. A device for performing in eye test as in claim 1, wherein said computer can measure light refraction to determine an eye prescription for said user.

6. A device for performing in eye test as in claim 1, wherein said display can display pictures in 3 dimensions.

7. A device for performing in eye test as in claim 1, wherein said computer can operate in at least Macintosh/UNIX, Windows and Linux.

* * * * *

UNITED STATES PATENT AND TRADEMARK OFFICE
CERTIFICATE OF CORRECTION

PATENT NO. : 7,350,921 B2
APPLICATION NO. : 10/805633
DATED : April 1, 2008
INVENTOR(S) : Ridings Page 1 of 1

It is certified that error appears in the above-identified patent and that said Letters Patent is hereby corrected as shown below:

Title Page, Item (57) Abstract:

Delete Abstract and replace with new Abstract as follows:

-- A device for performing in eye test includes a display for animated visual acuity letters and scalable dynamic letters, a computer to control the display and to link to a patient database, and the display having at least a contrast sensitivity or 400:1 or greater, a true rez visual acuity letter of 1°, a screen resolution of 1024 x 768 or greater under an ambient light (greater) > 4500K. --.

Signed and Sealed this

Seventeenth Day of June, 2008

JON W. DUDAS
*Director of the United States Patent and Trademark Office*